United States Patent
Genung et al.

(10) Patent No.: US 12,421,224 B2
(45) Date of Patent: Sep. 23, 2025

(54) AZETIDINYL O-GLYCOPROTEIN-2-ACETAMIDO-2-DEOXY-3-D-GLUCOPYRANOSIDASE INHIBITORS

(71) Applicant: BIOGEN MA INC., Cambridge, MA (US)

(72) Inventors: Nathan Genung, Charlestown, MA (US); Kevin M. Guckian, Northborough, MA (US); Jeffrey Vessels, Marlborough, MA (US); Lei Zhang, Westford, MA (US); Ryan Gianatassio, Everett, MA (US); Edward Yin Shiang Lin, Ashland, MA (US); Zhili Xin, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 1030 days.

(21) Appl. No.: 17/435,125

(22) PCT Filed: Mar. 6, 2020

(86) PCT No.: PCT/US2020/021479
§ 371 (c)(1),
(2) Date: Aug. 31, 2021

(87) PCT Pub. No.: WO2020/185593
PCT Pub. Date: Sep. 17, 2020

(65) Prior Publication Data
US 2022/0259197 A1    Aug. 18, 2022

Related U.S. Application Data

(60) Provisional application No. 62/815,553, filed on Mar. 8, 2019.

(51) Int. Cl.
*C07D 417/14*    (2006.01)
*C07D 495/04*    (2006.01)

(52) U.S. Cl.
CPC ......... *C07D 417/14* (2013.01); *C07D 495/04* (2013.01)

(58) Field of Classification Search
CPC ............................ C07D 417/14; C07D 495/04
See application file for complete search history.

(56) References Cited

U.S. PATENT DOCUMENTS 9,879,001 B2 * 1/2018 Yu .................... C07D 417/14

FOREIGN PATENT DOCUMENTS

| JP | 2016-517411 A | 6/2016 |
| WO | 2014/159234 A1 | 10/2014 |
| WO | 2018/109202 A1 | 6/2018 |
| WO | 2018/154133 A1 | 8/2018 |

OTHER PUBLICATIONS

International Search Report and Written Opinion for Application No. PCT/US2020/021479, dated Jun. 2, 2020, 16 pages.
Nozaki et al., Medicinal Chemistry, First Edition. Kagaku-Dojin Publishing Company, Inc. pp. 98-99, (1995).
Wermuth, Transformation of Molecules Based on Equivalent Transposition. The Practice of Medicinal Chemistry. Technomic Co., Ltd. Chapter 13, pp. 235-271. Aug. 15, 2010.
Japanese Office Action for Application No. 2021-552999, dated Mar. 13, 2024, 6 pages.

* cited by examiner

*Primary Examiner* — Rebecca L Anderson
(74) *Attorney, Agent, or Firm* — McCarter & English, LLP; Xin Zhang; Zhongyu Wang

(57) ABSTRACT

Described herein are compounds represented by formula (I) (I) or a pharmaceutically acceptable salt thereof, pharmaceutical compositions comprising the same and methods of preparing and using the same. The variables Ar, X, $R^1$, $R^3$, $R^4$, $Y^1$, $Y^2$, and Z are as defined herein.

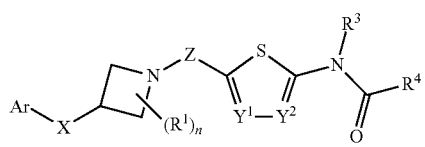

20 Claims, No Drawings

AZETIDINYL O-GLYCOPROTEIN-2-ACETAMIDO-2-DEOXY-3-D-GLUCOPYRANOSIDASE INHIBITORS

RELATED APPLICATIONS

This application is a 35 U.S.C. § 371 national stage filing of International Application No. PCT/US2020/021479, filed on Mar. 6, 2020, which in turn claims the benefit of the filing date, under 35 U.S.C. § 119(e), of U.S. Provisional Application No. 62/815,553, filed on Mar. 8, 2019. The entire contents of the aforementioned applications which are incorporated herein by reference.

BACKGROUND

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This monosaccharide is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-glycoprotein-2-acetamido-2-deoxy-3-D-glucopyranosidase or O-GlcNAcase or OGA, removes this post-translational modification to liberate proteins, making the O-GlcNAc-modification a dynamic cycle occurring several times during the lifetime of a protein.

O-GlcNAc-modified proteins regulate a wide range of vital cellular functions including, e.g., transcription, proteasomal degradation and cellular signaling. O-GlcNAc is also found on many structural proteins, including the cytoskeletal protein "tau" which is responsible for stabilizing a key cellular network of microtubules that is essential for distributing proteins and nutrients within neurons. Importantly, tau has been clearly implicated in the etiology of several diseases including tauopathies, Alzheimer's disease, Parkinson's disease, dementia and cancer.

It is well established that Alzheimer's disease and a number of related tauopathies including Progressive Supranuclear Palsy (PSP) and amyotrophic lateral sclerosis (ALS) are characterized, in part, by the development of neurofibrillary tangles (NFTs). These NFTs are aggregates of paired helical filaments (PHFs) and are composed of an abnormal form of tau. In AD patients, tau becomes hyperphosphorylated, thereby disrupting its normal function, forming PHFs and ultimately aggregating to form NFTs.

Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups.

It has recently emerged that increases in phosphorylation levels result in decreased O-GlcNAc levels and conversely, increased O-GlcNAc levels correlate with decreased phosphorylation levels. It has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase, which prevents hyperphosphorylation of tau by preventing removal of O-GlcNac from tau, should compensate for the age-related impairment of glucose metabolism within the brains of health individuals as well as patients suffering from Alzheimer's disease or related neurodegenerative diseases.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

In view of foregoing technical challenge, and given the potential for regulation of O-GlcNAcase for treatment of AD, tauopathies and other neurological diseases, there remains a need for development of potent and selective O-GlcNAcase inhibitors.

SUMMARY

Described herein are compounds that are useful treating various diseases, disorders and medical conditions, including but not limited to those associated with proteins that are modified by O-GlcNAcase.

A first embodiment of a compound of the present invention is represented by the following structural formula:

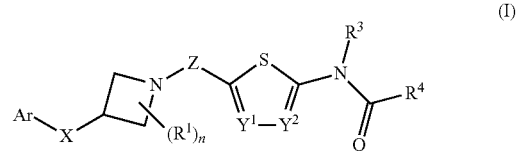

(I)

or a pharmaceutically acceptable salt thereof, wherein:
Ar is an optionally substituted 6- to 10-membered aryl or an optionally substituted 5- to 10-membered heteroaryl; provided that when X is absent, Ar is not phenyl;
X is absent, $—CR^2R^2—$, $—(CR^2R^2)_2—$, $—O—$, $—(CR^2R^2)O—$, $—O(CR^2R^2)—$, $—NR^d—$, $—NR^d(CR^2R^2)—$, or $—(CR^2R^2)NR^d—$;
$Y^1$ and $Y^2$ are each $CR^c$ or N, wherein at least one of $Y^1$ or $Y^2$ is N;
Z is $—CR^2R^2—$, $—C(\!=\!O)—$, $—(CR^2R^2)_2—$, or $—CH_2C(\!=\!O)—$;
$R^c$ is —H, halo, $—C_1-C_4$ alkyl, or $—C_1-C_4$ haloalkyl;
$R^d$ is —H, $—C_1-C_4$ alkyl, $—C_1-C_4$ haloalkyl, or $—C(\!=\!O)C_1-C_4$ alkyl;
n is 0 or an integer from 1 to 5;
when n is other than 0, $R^1$, for each occurrence, is independently halo, $—C_1-C_4$ alkyl, $—C_1-C_4$ haloalkyl, or $—C_1-C_4$ alkoxy;
$R^2$, for each occurrence, is independently —H, halo, $—C_1-C_4$ alkyl, $—C_1-C_4$ haloalkyl, $—C_3-C_{10}$ cycloalkyl, or $—C_3-C_{10}$ halocycloalkyl;
or alternatively two $R^2$ together with the carbon atom to which they are attached form a $—C_3-C_{10}$ cycloalkyl;
$R^3$ is H or $—C_1-C_4$ alkyl; and
$R^4$ is —H, $—C_1-C_4$ alkyl, $—C_1-C_4$ haloalkyl, or $—C_3-C_6$ cycloalkyl;

or alternatively R³ and R⁴ taken together with their intervening atoms form an optionally substituted 5- to 7-membered heterocyclyl.

Provided is a pharmaceutical composition comprising at least one compound described herein, or a pharmaceutically acceptable salt thereof, and at least one pharmaceutically acceptable excipient.

Also provided is a method of treating a subject with a disease or condition selected from a neurodegenerative disease, a tauopathy, diabetes, cancer and stress, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of inhibiting O-GlcNAcase in a subject in need thereof, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of treating a disease or condition characterized by hyperphosphorylation of tau in the brain, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient. In one embodiment, the disease or condition characterized by hyperphosphorylation of tau in the brain is Alzheimer's disease.

DETAILED DESCRIPTION

Described herein are compounds that are useful treating various diseases, disorders and medical conditions, including but not limited to those associated with proteins that are modified by O-GlcNAcase.

In a first embodiment, a compound of the present invention is represented by the following structural formula (I):

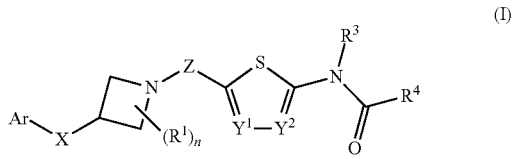

or a pharmaceutically acceptable salt thereof, wherein the variables are as defined above in the summary for a compound represented by formula (I) or a pharmaceutically acceptable salt thereof.

In a second embodiment, a compound of the present invention is represented by the following structural formula (II):

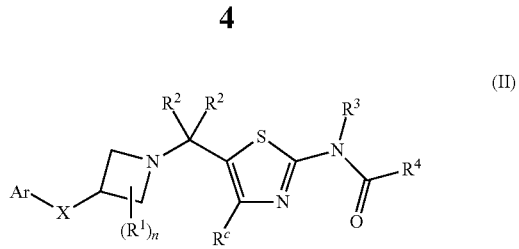

or a pharmaceutically acceptable salt thereof; wherein the remaining variables are as defined in the first embodiment.

In a third embodiment, a compound of the invention is represented by the following structural formula (III):

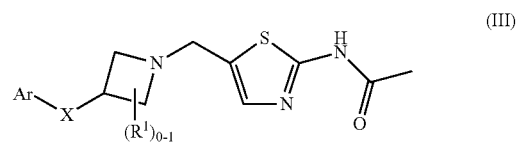

or a pharmaceutically acceptable salt thereof; wherein the remaining variables are as defined in the first or second embodiments.

In a fourth embodiment, a compound of the invention is represented by one of the following structural formulas (IV-A) and (IV-B):

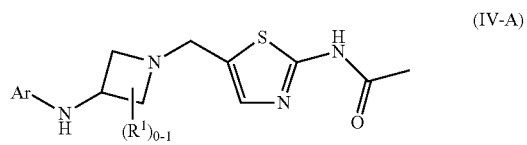

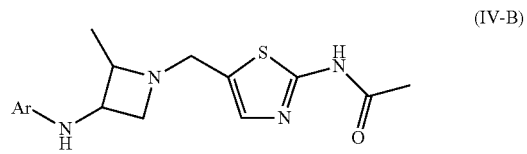

or a pharmaceutically acceptable salt thereof; wherein the remaining variables are as defined in the first, second, or third embodiments.

In a fifth embodiment, a compound of the invention is represented by the following structural formula (V):

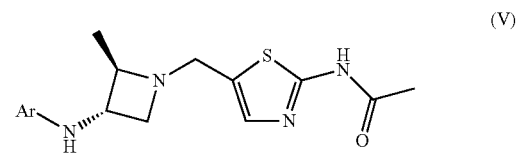

or a pharmaceutically acceptable salt thereof; wherein $R^1$ is —$C_1$-$C_4$ alkyl and wherein $R^2$ is —H, —$CH_3$ or —$CH_2CH_3$; and wherein the remaining variables are as defined in the first, second, or third embodiment.

In a sixth embodiment, in a compound of the invention in accordance to the first, second, or third embodiments, or a pharmaceutically acceptable salt thereof, X is —$CR^2R^2$—, —($CR^2R^2$)O—, —$NR^d$—, or —$NR^d(CR^2R^2)$—; wherein $R^d$ is —H or —$C_1$-$C_4$ alkyl.

In a seventh embodiment, in a compound of the invention in accordance to the first or second embodiments, or a pharmaceutically acceptable salt thereof, $R^c$ is —H or halo and $R^4$ is —H and —$C_1$-$C_4$ alkyl.

In an eighth embodiment, in a compound of the invention in accordance to the first, second, third, fourth, fifth, sixth, or seventh embodiments, or a pharmaceutically acceptable salt thereof, Ar is an optionally substituted 5- to 10-membered heteroaryl.

In an ninth embodiment, in a compound of the invention in accordance to the first, second, third, fourth, fifth, sixth, seventh, or eighth embodiments, or a pharmaceutically acceptable salt thereof, Ar is an optionally substituted 5- or 6-membered monocyclic heteroaryl.

In a tenth embodiment, in a compound of the invention in accordance to the first, second, third, fourth, fifth, sixth, seventh, eighth, or ninth embodiments, or a pharmaceutically acceptable salt thereof, Ar is an optionally substituted 6-membered monocyclic heteroaryl.

In an eleventh embodiment, in a compound of the invention in accordance to the first, second, third, fourth, fifth, sixth, seventh, eighth, ninth, or tenth embodiments, or a pharmaceutically acceptable salt thereof, Ar is an optionally substituted pyridinyl, an optionally substituted pyrimidinyl, or an optionally substituted pyrazinyl.

In a twelfth embodiment, in a compound of the invention in accordance to the first, second, third, fourth, fifth, sixth, seventh embodiments, or a pharmaceutically acceptable salt thereof, Ar is an optionally substituted

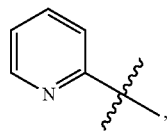 [SMILES: *c1ccccn1]

an optionally substituted

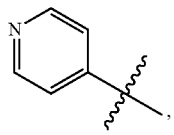

an optionally substituted

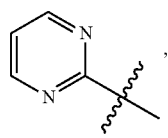

an optionally substituted

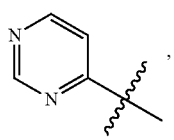

an optionally substituted

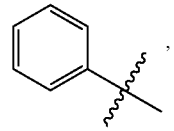 [SMILES: *c1ccccc1]

an optionally substituted

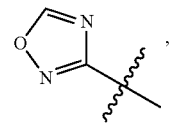

or an optionally substituted

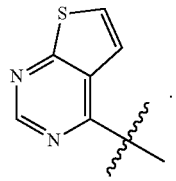

In a thirteenth embodiment, in a compound of the invention in accordance to the first, second, third, fourth, fifth, sixth, seventh, eighth, ninth, tenth, eleventh, or twelfth embodiments, or a pharmaceutically acceptable salt thereof, Ar is an optionally substituted

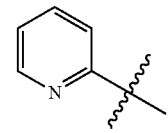 [SMILES: *c1ccccn1]

or an optionally substituted

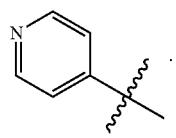

In a fourteenth embodiment, in a compound of the invention in accordance to the first, second, third, fourth, fifth, sixth, seventh, eighth, ninth, tenth, eleventh, twelfth, thirteenth embodiments, or a pharmaceutically acceptable salt thereof, wherein Ar is optionally substituted with one or more groups selected from $C_1$-$C_4$ alkyl, $C_1$-$C_4$ haloalkyl, $C_3$-$C_6$ cycloalkyl, $C_3$-$C_6$ heterocyclyl, halo, —CN, —NO$_2$, —OR$^z$, —NR$^x$R$^y$, —S(O)$_i$R$^x$, —NR$^x$S(O)$_i$R$^y$, —S(O)$_i$N-R$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, phenyl and monocyclic heteroaryl;

wherein
the $C_1$-$C_4$ alkyl group substituent on Ar is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^y$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy);

the $C_3$-$C_6$ cycloalkyl, $C_3$-$C_6$ heterocyclyl, phenyl and monocyclic heteroaryl group substituent on Ar are optionally and independently substituted with $C_1$-$C_4$ alkyl, $C_1$-$C_4$ haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$;

each R$^x$ and each R$^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by R$^x$ or R$^y$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy or halomethoxy);

R$^z$ is —H, $C_1$-$C_4$ alkyl, $C_1$-$C_4$ alkoxy, $C_3$-$C_8$ cycloalkyl, or $C_3$-$C_8$ heterocyclyl; wherein the $C_1$-$C_4$ alkyl or $C_3$-$C_8$ cycloalkyl group represented by R$^z$ is optionally substituted with one or more substituents selected from —CN, halo, hydroxyl, $C_1$-$C_4$ alkyl, $C_1$-$C_4$ alkoxy, $C_3$-$C_6$ cycloalkyl and phenyl (optionally substituted with one or more groups selected from —CH$_3$, halomethyl, halo, methoxy and halomethoxy); and i is 0, 1, or 2.

In a fifteenth embodiment, in a compound of the invention in accordance to the first, second, third, fourth, fifth, sixth, seventh, eighth, ninth, tenth, eleventh, twelfth, thirteenth, or fourteenth embodiments, or a pharmaceutically acceptable salt thereof, Ar is optionally substituted with one with one or more groups selected from $C_1$-$C_4$ alkyl, $C_1$-$C_4$ haloalkyl, halo, —CN, —NO$_2$, —OR$^z$, —SR$^z$, —NR$^x$S(O)$_i$R$^y$, —C(=O)OR$^x$, —OC(=O)OR$^x$, —C(=S)OR$^y$, —O(C=S)R$^x$, —C(=O)NR$^x$R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^x$; wherein each R$^x$, each R$^y$ and R$^z$ each is independently —H or $C_1$-$C_4$ alkyl.

In a sixteenth embodiment, in a compound of the invention in accordance to the first, second, third, fourth, fifth, sixth, seventh, eighth, ninth, tenth, eleventh, twelfth, thirteenth, fourteenth, or fifteenth embodiments, or a pharmaceutically acceptable salt thereof, Ar is optionally substituted with one with one or more groups selected from $C_1$-$C_4$ alkyl, $C_1$-$C_4$ haloalkyl, halo, —CN, —OR$^z$, and —C(=O)NR$^x$R$^y$.

In a seventeenth embodiment, in a compound of the invention in accordance to the first, second, third, fourth, fifth, sixth, seventh, eighth, ninth, tenth, eleventh, twelfth, thirteenth, fourteenth, fifteenth, or sixteenth embodiments, or a pharmaceutically acceptable salt thereof, Ar is optionally substituted with one with one or more groups selected from —CH$_3$, —F, —CN, and —OCH$_3$.

In another embodiment, a compound of the invention is selected from the compounds described in the exemplifications herein. Pharmaceutically acceptable salts thereof as well as the neutral forms are included.

As used herein, the term "alkyl" refers to a fully saturated branched or straight chained hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkoxy" refers to the group —OR, in which R is an alkyl or a cycloalkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopropyl, —O-cyclobutyl, —O-cyclopentyl and —O-cyclohexyl.

As used herein, the terms "aryl", "aryl group", "aryl ring", "aromatic group" and "aromatic ring" are used interchangeably to refer to an aromatic 6- to 12-membered monocyclic or bicyclic carbon ring system. Examples of monocyclic aromatic ring systems include, but are not limited to, phenyl, and the like. Examples of bicyclic aromatic ring systems include, but are not limited to, naphthyl, and the like. As used herein, a bicyclic aryl or a bicyclic aromatic ring system includes bicyclic ring systems where a monocyclic aryl fused to another monocyclic aryl, and bicyclic ring systems where a monocyclic aryl is fused to a monocyclic cycloaliphatic ring.

The number of carbon atoms in a group is specified herein by the prefix "$C_{x\text{-}xx}$", wherein x and xx are integers. For example, "$C_{1\text{-}4}$ alkyl" is an alkyl group which has from 1 to 4 carbon atoms.

As used herein, the term "halogen" or "halo" may be fluoro, chloro, bromo or iodo.

As used herein, the term "haloalkyl" refers to an alkyl, as defined herein, that is substituted by one or more halo groups as defined herein.

As used herein, the terms "cycloaliphatic", "cycloaliphatic group" or "cycloaliphatic ring" are used interchangeably to refer to a saturated (i.e., a cycloalkyl that is also defined below), unsaturated non-aromatic, monocyclic or bicyclic carbon ring system which has 3- to 12-ring members. Examples of monocyclic cycloaliphatic ring systems include, but are not limited to, cyclopropyl, cyclopentenyl, and the like. Examples of bicyclic cycloaliphatic ring systems include, but are not limited to octahydronapthalenyl, decalinyl, and the like.

As used herein, the terms "heterocyclyl", "heterocyclyl group", "heterocyclic" and "heterocyclic ring" are used interchangeably to refer to a saturated, unsaturated non-aromatic, monocyclic or bicyclic ring system which has from 3- to 12-ring members, or in particular 3- to 6-ring members or 5- to 7-ring members, at least one of which is a heteroatom, and up to 4 (e.g., 1, 2, 3 or 4) of which may be heteroatoms, wherein the heteroatoms are independently selected from O, S and N, and wherein C can be oxidized (e.g., C(=O)), N can be oxidized (e.g., N(O)) or quaternized (e.g. $N^+$), and S can be optionally oxidized to sulfoxide and sulfone. Examples of monocyclic heterocyclic ring systems include aziridinyl, azetidinyl, oxetanyl, thietanyl, pyrrolidinyl, tetrahydrofuranyl, thiolanyl, imidazolidinyl, pyrazolidinyl, isoxazolidinyl, isothiazolidinyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, hydantoinyl, pyrrolidinonyl, tetrahydrothiopyranyl, tetrahydropyridinyl, and thiopyranyl, and the like. Examples of bicyclic heterocyclic ring systems include benzo[1,3]dioxolyl, tetrahydroindolyl, and 2-azaspiro[3.3]heptanyl, and the like. As used herein, a bicyclic heterocyclyl or a bicyclic heterocyclic ring system includes bicyclic ring systems where a monocyclic heterocyclyl is fused to another monocyclic heterocyclyl; bicyclic ring systems where a monocyclic heterocyclyl is fused to a cycloaliphatic ring, and bicyclic ring systems where a monocyclic heterocyclyl is fused to a phenyl ring.

As used herein, the terms "heteroaryl", "heteroaryl group", "heteroaromatic" and "heteroaromatic ring" are used interchangeably to refer to an aromatic 5- to 12-membered monocyclic or bicyclic ring system, having 1 to 4 heteroatoms independently selected from O, S and N, and wherein N can be oxidized (e.g., N(O)) or quaternized, and S can be optionally oxidized to sulfoxide and sulfone. "Heteroaryl" includes a heteroaromatic ring that is fused to another heteroaromatic ring, a heteroaromatic ring that is fused to a phenyl ring, a heteroaromatic ring that is fused to a cycloaliphatic ring, or a heteroaromatic ring that is fused to non-aromatic heterocyclic ring such as tetrahydrofuran, pyran, pyrrolidine, piperidine, and the like. As used herein, the heteroaryl group Ar can be attached to the rest of a compound of the invention at any ring that has an open valency. Non-limiting examples of monocyclic heteroaromatic ring systems includepyrrolyl, furanyl, imidazolyl, pyrazolyl, oxazolyl, isoxazolyl, thiazolyl, isothiazolyl, oxadiazolyl, thiadiazolyl, triazolyl, tetrazolyl, pyridyl, pyrazinyl, pyrimidyl, pyridazinyl, triazinyl, tetrazinyl, 1-oxopyridyl, thienyl, etc. Non-limiting examples of bicyclic heteroaromatic ring systems include azaindolyl, benzimidazolyl, benzofuryl, benzoisoxazolyl, benzoisothiazolyl, benzothiadiazolyl, benzothiazolyl, benzothienyl, benzotriazolyl, benzoxadiazolyl, benzoxazolyl, cyclopentaimidazolyl, cyclopentatriazolyl, furopyridinyl, imidazopyridyl, imidazopyrimidinyl, indazolyl, indolizinyl, indolyl, isoquinolinyl, oxazolopyridinyl, purinyl, pyrazolopyrimidinyl, pyrazolopyrazinyl, pyridopyazinyl, pyridopyrimidinyl, pyrrolo[2,3]pyrimidinyl, pyrrolopyrazolyl, pyrroloimidazolyl, pyrrolotriazolyl, quinazolinyl, quinoxalinyl, quinolinyl, isoquinolinyl, thiazolopyridinyl, thienopyridinyl, thienopyrimidinyl, thienopyrazinyl, napthyridyl, and the like. As used herein, the term "cycloalkyl" refers to completely saturated monocyclic or bicyclic (e.g., fused) hydrocarbon groups of 3-12 carbon atoms, 3-6 carbon atoms or 5-7 carbon atoms.

As used herein, the term "halocycloalkyl" refers to a cycloalkyl, as defined herein, that is substituted by one or more halo groups as defined herein.

A substituted alkyl, phenyl, heteroaryl, non-aromatic heterocyclyl or heterocyclyl group is an alkyl, phenyl, heteroaryl, non-aromatic heterocyclyl or heterocyclyl group that has one or more substituents. Suitable substituents are those that do not significantly decrease the O-GlcNAcase inhibitory activity of a compound of formula (I), (II), (III), (IV), (V) (hereinafter collectively a compound of any one of formulas (I) through (V)), or a pharmaceutically acceptable salt thereof. Examples of suitable substituents for an alkyl, phenyl, heteroaryl, non-aromatic heterocyclyl or heterocyclyl group include but are not limited to $C_1$-$C_4$ alkyl, $C_1$-$C_4$ haloalkyl, $C_3$-$C_6$ cycloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, phenyl and monocyclic heteroaryl. The $C_1$-$C_4$ alkyl group substituent is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^x$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy). The $C_3$-$C_6$ cycloalkyl, phenyl and monocyclic heteroaryl group substituents are optionally and independently substituted with $C_1$-$C_4$ alkyl, $C_1$-$C_4$haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^x$. In these substituents, each R$^x$ and each R$^y$ is independently —H, —$C_1$-$C_4$ alkyl, or $C_3$-$C_8$ cycloalkyl, where the $C_1$-$C_4$ alkyl or $C_3$-$C_8$ cycloalkyl represented by R$^x$ or R$^y$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy or halomethoxy). In these substituents, R$^z$ is —H, —$C_1$-$C_4$ alkyl, or $C_3$-$C_8$ cycloalkyl, where the $C_1$-$C_4$ alkyl or $C_3$-$C_8$ cycloalkyl group represented by R$^z$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy and halomethoxy). In these substituents, i is 0, 1, or 2.

Pharmaceutically acceptable salts of the compounds disclosed herein are also included in the invention. In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate or α-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid; affording a physiologically acceptable anion. Alkali metal (for example, sodium, potassium or lithium) or alkaline earth metal (for example calcium) salts of carboxylic acids can also be made.

Pharmaceutically acceptable base addition salts can be prepared from inorganic and organic bases. Suitable bases include but are not limited to alkali metal hydroxides, alkaline earth metal hydroxides, carbonates, bicarbonates, and the like.

Some of the disclosed compounds, or pharmaceutically acceptable salts thereof, contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis or chromatographic separation using a chiral stationary phase). The disclosed compounds may exist in tautomeric forms and mixtures and separate individual tautomers are contemplated. In addition, some compounds may exhibit polymorphism.

When a particular steroisomer (e.g., enantiomer, diasteromer, etc.) of a compound used in the disclosed methods is depicted by name or structure, the stereochemical purity of the compounds is at least 60%, 70%, 80%, 90%, 95%, 97%, 99%, 99.5% or 99.9%. "Stererochemical purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In one embodiment, any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

One aspect of the invention includes a method for inhibiting a glycosidase and/or a glycosidase signaling pathway in a cell, the method comprising contacting the cell with an effective amount of a compound of any one of formulas (I) through (V), or a pharmaceutically acceptable salt thereof. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase. In one embodiment, the cell is contacted in vitro or in vivo. In one embodiment, contacting the cell includes administering the compound to a subject.

One aspect of the invention includes a method for inhibiting a glycosidase and/or a glycosidase signaling pathway in a subject in need thereof, the method comprising administering to the subject, a therapeutically effective amount of a compound of any one of formulas (I) through (V), or a pharmaceutically acceptable salt thereof, thereby activating the glycosidase in the subject. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase.

One aspect of the invention includes a method for promoting survival of a eukaryotic cell (e.g., a mammalian cell) or increasing the lifespan of the cell, the method comprising administering to the subject a therapeutically effective amount of a compound of any one of formulas (I) through (V), or a pharmaceutically acceptable salt thereof, thereby promoting survival of the eukaryotic cell or increasing lifespan of the cell.

One aspect of the invention includes a method for treating a disease or a condition that is caused, mediated and/or propagated by O-GlcNAcase activity in a subject, the method comprising administering to the subject a therapeutically effective amount of a compound of any one of formulas (I) through (V), or a pharmaceutically acceptable salt thereof. Preferably, the disease or condition is a neurological disorder, diabetes, cancer or stress. More preferably, the disease or condition is a neurological disorder. In one embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CIDP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic, stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis, Tangle-only dementia, Huntington's disease, and Parkinson's disease. In another embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, mild cognitive impairment (MCI), Huntington's disease, and Parkinson's disease. In yet another embodiment, the neurological disorder is Alzheimer's disease.

One aspect of the invention includes a method for treating a disease or a condition that is characterized by hyperphosphorylation of tau (e.g., hyperphosphorylation of tau in the brain) in a subject, the method comprising administering to the subject a therapeutically effective amount of a compound of any one of formulas (I) through (V), or a pharmaceutically acceptable salt thereof. In one embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-panto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-OlszeWski syndrome, Subacute sclerosing panencephalitis, Tangle-only dementia, Huntington's disease, and Parkinson's disease. In another embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, ischemic stroke, mild cognitive impairment (MCI), Huntington's disease, and Parkinson's disease. In yet another embodiment, the disease or condition is Alzheimer's disease.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: reducing the extent of the disease, disorder or syndrome; ameliorating or improving a clinical symptom or indicator associated with the disorder; and delaying, inhibiting or decreasing the likelihood of the progression of the disease, disorder or syndrome.

The term "an effective amount" means an amount of a compound of any one of formulas (I) through (V), or a pharmaceutically acceptable salt thereof, e.g., 0.1 mg to 1000 mg/kg body weight, when administered to a subject, which results in beneficial or desired results, including clinical results, i.e., reversing, alleviating, inhibiting, reducing or slowing the progression of a disease or condition treatable by a compound of any one of formulas (I) through (V), or a pharmaceutically acceptable salt thereof, reducing the likelihood of recurrence of a disease or condition treatable by a compound of any one of formulas (I) through (V), or a pharmaceutically acceptable salt thereof or one or more symptoms thereof, e.g., as determined by clinical symptoms, compared to a control. The expression "an effective amount" also encompasses the amounts which are effective for increasing normal physiological function, for example, between 0.01 mg/kg per day to 500 mg/kg per day.

Another embodiment of the present invention is a pharmaceutical composition comprising at least one compound described herein, or a pharmaceutically acceptable salt thereof, and at least one pharmaceutically acceptable carrier.

Also included are the use of a compound of any one of formulas (I) through (V), or a pharmaceutically acceptable salt thereof in the manufacture of a medicament for the treatment of one or more diseases or conditions described herein. Also included herein are pharmaceutical compositions comprising a compound of any one of formulas (I) through (V), or a pharmaceutically acceptable salt thereof optionally together with a pharmaceutically acceptable carrier, in the manufacture of a medicament for the treatment of one or more diseases or conditions described herein. Also included is a compound of any one of formulas (I) through (V), or a pharmaceutically acceptable salt thereof for use the treatment of a subject with one or more diseases or conditions described herein. Further included are pharmaceutical compositions comprising a compound of any one of formulas (I) through (V), or a pharmaceutically acceptable salt thereof, optionally together with a pharmaceutically acceptable carrier, for use in the treatment of one or more diseases or conditions described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

A compound of any one of formulas (I) through (V), or a pharmaceutically acceptable salt thereof, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

EXEMPLIFICATIONS

General Methods

Chromatography on silica gel was carried out using 20-40 uM (particle size), 250-400 mesh, or 400-632 mesh silica gel using either a Teledyne ISCO Combiflash RF or a Grace Reveleris X2 with ELSD purification systems.

Analytical HPLC

Acidic HPLC: Conducted on a Shimadzu 20A instrument with an Ultimate C18 3.0×50 mm, 3 um column eluting with 2.75 mL/4 L TFA in water (solvent A) and 2.5 mL/4 L TFA in acetonitrile (solvent B) by the following methods:

Method A: using the following elution gradient 0%-60% (solvent B) over 6 minutes and holding at 60% for 2 minutes at a flow rate of 1.2 ml/minutes. Wavelength: UV 220 nm, 215 nm and 254 nm.

Method B: using the following elution gradient 10%-80% (solvent B) over 6 minutes and holding at 60% for 2 minutes at a flow rate of 1.2 ml/minutes. Wavelength: UV 220 nm, 215 nm and 254 nm.

Method C: using the following elution gradient 30%-90% (solvent B) over 6 minutes and holding at 60% for 2 minutes at a flow rate of 1.2 ml/minutes. Wavelength: UV 220 nm, 215 nm and 254 nm.

Basic HPLC: Conducted on a Shimadzu 20A instrument with Xbrige Shield RP-18, 5um, 2.1×50 mm column eluting with 2 mL/4 L $NH_3H_2O$ in water (solvent A) and acetonitrile (solvent B), by the following methods:

Method D: using the following elution gradient 0%-60% (solvent B) over 4.0 minutes and holding at 60% for 2 minutes at a flow rate of 1.2 ml/minutes.

Method E: using the following elution gradient 10%-80% (solvent B) over 4.0 minutes and holding at 60% for 2 minutes at a flow rate of 1.2 ml/minutes.

Method F: using the following elution gradient 30%-90% (solvent B) over 4.0 minutes and holding at 60% for 2 minutes at a flow rate of 1.2 ml/minutes.

Analytical LCMS

Acidic LCMS: Conducted on a Shimadzu 2010 Series, Shimadzu 020 Series, or Waters Acquity UPLC BEH. (MS ionization: ESI) instrument equipped with a C18 column (2.1 mm×30 mm, 3.0 mm or 2.1 mm×50 mm, C18, 1.7 um), eluting with 1.5 mL/4 L TFA in water (solvent A) and 0.75 mL/4 LTFA in acetonitrile (solvent B) using the methods below:

1.5 Minute Methods

General method: using the following elution gradient 5%-95% (solvent B) over 0.7 minutes and holding at 95% for 0.4 minutes at a flow rate of 1.5 ml/minutes. Wavelength: UV 220 nm and 254 nm.

2 Minute Methods

Method A: using the following elution gradient 0%-60% (solvent B) over 0.9 minutes and holding at 60% for 0.6 minutes at a flow rate of 1.2 ml/minutes. Wavelength: UV 220 nm and 254 nm.

Method B: using the following elution gradient 10%-80% (solvent B) over 0.9 minutes and holding at 60% for 0.6 minutes at a flow rate of 1.2 ml/minutes. Wavelength: UV 220 nm and 254 nm.

Method C: using the following elution gradient 30%-90% (solvent B) over 0.9 minutes and holding at 60% for 0.6 minutes at a flow rate of 1.2 ml/minutes. Wavelength: UV 220 nm and 254 nm.

3.5 Minute Method

Initial conditions, solvent A-95%: solvent B-5%; hold at initial from 0.0-0.1 min; Linear Ramp to solvent A-5%: solvent B-95% between 0.1-3.25 min; hold at solvent A-5%: solvent B-95% between 3.25-3.5 min. Diode array/MS detection.

4 Minute Methods

Method A: using the following elution gradient 0%-60% (solvent B) over 3 minutes and holding at 60% for 0.5 minutes at a flow rate of 0.8 ml/minutes. Wavelength: UV 220 nm and 254 nm.

Method B: using the following elution gradient 10%-80% (solvent B) over 3 minutes and holding at 60% for 0.5 minutes at a flow rate of 0.8 ml/minutes. Wavelength: UV 220 nm and 254 nm.

Method C: using the following elution gradient 30%-90% (solvent B) over 3 minutes and holding at 60% for 0.5 minutes at a flow rate of 0.8 ml/minutes. Wavelength: UV 220 nm and 254 nm.

7 Minute Methods

Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-900% (solvent B) over 6 minutes and holding at 60% for 0.5 minutes at a flow rate of 0.8 ml/minutes. Wavelength: UV 220 nm and 254 nm.

Basic LCMS

Conducted on a Shimadzu2020 Series or Waters Acquity UPLC BEH (MS ionization: ESI) instrument equipped with XBridge Shield RP18, 5 um column (2.1 mm×30 mm, 3.0 mm i.d.) or 2.1 mm×50 mm, C18, 1.7 um column, eluting with 2 mL/4 L $NH_3 \cdot H_2O$ in water (solvent A) and acetonitrile (solvent B) using the methods below:

3 Minute Methods

Method A: using the following elution gradient 0%-60% (solvent B) over 2 minutes and holding at 60% for 0.48 minutes at a flow rate of 1 ml/minutes. Wavelength: UV 220 nm and 254 nm.

Method B: using the following elution gradient 10%-80% (solvent B) over 2 minutes and holding at 60% for 0.48 minutes at a flow rate of 1 ml/minutes. Wavelength: UV 220 nm and 254 nm.

Method C: using the following elution gradient 30%-90% (solvent B) over 2 minutes and holding at 60% for 0.48 minutes at a flow rate of 1 ml/minutes. Wavelength: UV 220 nm and 254 nm.

3.5 Minute Method

Initial conditions, solvent A-95%: solvent B-5%; hold at initial from 0.0-0.1 min; Linear Ramp to solvent A-5%: solvent B-95% between 0.1-3.25 min; hold at solvent A-5%: solvent B-95% between 3.25-3.5 min. Diode array/MS detection.

7 Minute Methods

Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-90% (solvent B) over 6 minutes and holding at 60% for 0.5 minutes at a flow rate of 0.8 ml/minutes. Wavelength: UV 220 nm and 254 nm.

SFC Analytical Separation

Instrument: Waters UPC2 analytical SFC (SFC—H). Column: ChiralCel OJ, 150×4.6 mm I.D., 3 μm. Mobile phase: A for CO2 and B for Ethanol (0.05% DEA). Gradient: B 40%. Flow rate: 2.5 mL/min. Back pressure: 100 bar. Column temperature: 35° C. Wavelength: 220 nm Preparative HPLC Purification General Method: Preparative HPLC was performed on a Gilson UV/VIS-156 with UV detection at 220/254 nm Gilson 281 automatic collection.

Acidic condition: Two acid grading systems used: Hydrochloride acid and Formic acid.

Method A: Hydrochloride acid: YMC-Actus Triart C18 150×30 mm×5 um, Gradient used 0-100% acetonitrile with water and corresponding acid (0.05% HCl).

Method B: Formic acid: Phenomenex Synergi C18 150×30 mm×4 um, Gradient used 0-100% acetonitrile with water and corresponding acid (0.225% formic acid), the gradient shape was optimized for individual separations.

Neutral condition: Xtimate C18 150×25 mm×5 um, Gradient used 0-100% (water (10 mM $NH_4HCO_3$)-ACN), the gradient shape was optimized for individual separations.

Basic condition: Waters Xbridge Prep OBD C18 150×30 10 um, Gradient used 0-100% water (0.04% $NH_3H_2O$+10 mM $NH_4HCO_3$)-acetonitrile, the gradient shape was optimized for individual separations.

Preparative HPLC-MS Purification

Columns Used

Acid: Waters SunFire Prep, C18 5 um, OBD 19×100 mm
Base: Waters XSelect CSH Prep C18 5 um OBD 19×100 mm Gradient Profile: 12 min Run: Initial conditions: A-95%: B-5%; hold at initial from 0.0-0.5 min; linear ramp from A-5% to variable B-% (typical range is from B-40% to B-75%) between 0.5-7.5 min; linear ramp from B-% to B-95% from 7.5-8.0 min; hold at A-5%:B-95% between 8.0-10.0 min; end of DAD/MS detection; linear ramp down to initial conditions between 10.0-10.5 min and hold at initial for 1.5 min.

Mobile Phase: Acid: A: 0.1% trifluoroacetic acid in water (v/v); Mobile phase B: 0.1% trifluoroacetic acid in acetonitrile (v/v). Base: A: 0.1% ammonia in water (v/v); Mobile phase B: 0.1% ammonia in acetonitrile (v/v)

Preparative SFC Purification

Instrument: MG III preparative SFC (SFC-1). Column: ChiralCel OJ, 250×30 mm I.D., 5 μm. Mobile phase: A for $CO_2$ and B for Ethanol (0.1% $NH_3H_2O$). Gradient: B 50%. Flow rate: 40 mL/min. Back pressure: 100 bar. Column temperature: 38° C. Wavelength: 220 nm. Cycle time: ~8 min.

$^1$H-NMR

The NMR spectra were recorded on Bruker Avance III HD 500 MHz, Bruker Avance III 500 MHz, Bruker Avance III 400 MHz, Varian-400 VNMRS, or Varian-400 MR. Chemical shifts are expressed in parts per million (ppm) units. Coupling constants (J) are in units of hertz (Hz). Splitting patterns describe apparent multiplicities and are designated as s (single), d (double), t (triplet), dd (double doublet), dt (double triplet), dq (double quartet), m (multiplet), br (broad).

The following general reaction Schemes 1-6 provide useful details for preparing the instant compounds. The requisite intermediates are in some cases commercially available or can be prepared according to literature procedures. The illustrative reaction schemes are not limited by the compounds listed or by any particular substituents employed for illustrative purposes substituent labeling (i.e. R groups) as shown in the reaction schemes do not necessarily correlate to that used in the claims and often, for clarity, a single substituent is shown attached to the compound where multiple substituents are allowed under the definitions of Formula (I) hereinabove.

Scheme 1

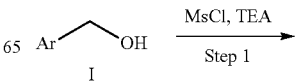

-continued

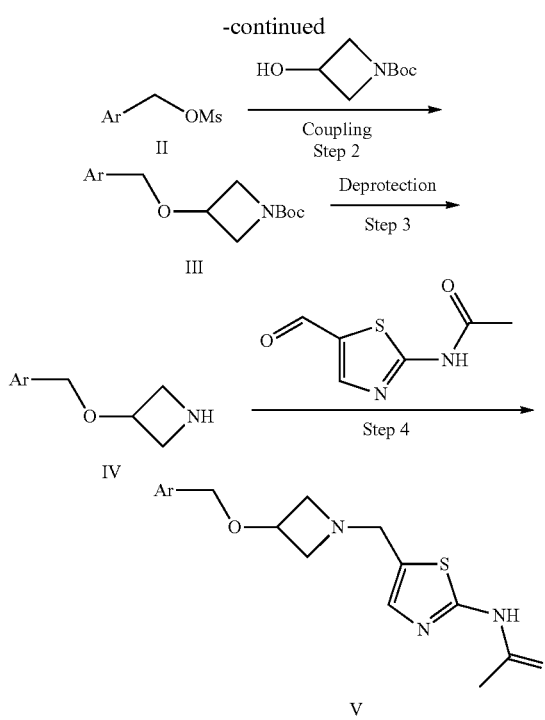

Intermediate 1

(2-methoxypyridin-4-yl)methyl methanesulfonate: Mesyl chloride (371.1 mg, 3.24 mmol, 250.77 uL, 1.5 eq.) was added dropwise to a mixture of (2-methoxypyridin-4-yl)methanol (300 mg, 2.16 mmol, 1 eq.) and triethylamine (437 mg, 4.32 mmol, 598.82 uL, 2 eq.) in CH₂Cl₂ (10 mL) at 0° C., then the mixture was stirred at 28° C. for 1 hr. TLC (Petroleum ether/EtOAc=1/1) showed the starting material was consumed completely. The mixture was concentrated to give compound (2-methoxypyridin-4-yl)methyl methanesulfonate (470 mg, crude) as a yellow solid, which was used directly in next step without further purification.

Intermediate 2

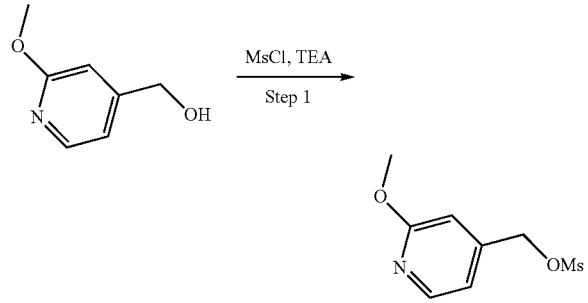

-continued

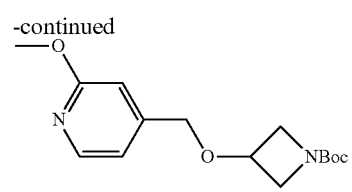

tert-butyl 3-((2-methoxypyridin-4-yl)methoxy)azetidine-1-carboxylate: NaH (173 mg, 4.32 mmol, 60% purity, 2 eq.) was added to a mixture of compound tert-butyl 3-hydroxyazetidine-1-carboxylate (411 mg, 2.38 mmol, 1.1 eq.) in DMF (10 mL) at 0° C., then the mixture was stirred at this temperature for 10 min., (2-methoxypyridin-4-yl)methyl methanesulfonate (470 mg, 2.16 mmol, 1 eq.) was added to the mixture at 0° C. and the mixture was stirred at 50° C. for 1 hr. TLC (Petroleum ether/EtOAc=1/1) showed the starting material was consumed completely. The mixture was quenched with aq. NH₄Cl (1 mL), concentrated and the residue was purified by Prep-TLC (Petroleum ether/EtOAc=1/1) to give tert-butyl 3-((2-methoxypyridin-4-yl)methoxy)azetidine-1-carboxylate (140 mg, 22% yield) as a yellow oil. LCMS (ESI): [M+H] 295. ¹HNMR: (400 MHz, CDCl₃) δ 8.13 (d, J=5.2 Hz, 1H), 6.82 (d, J=5.6 Hz, 1H), 6.70 (s, 1H), 4.41 (s, 2H), 4.30-4.33 (m, 1H), 4.06-4.11 (m, 2H), 3.94 (s, 3H), 3.87-3.90 (m, 2H), 1.44 (s, 9H).

Intermediate 3

3-((3-methoxybenzyl)oxy)azetidine: tert-butyl 3-((2-methoxypyridin-4-yl)methoxy)azetidine-1-carboxylate (140 mg, 475.62 μmol, 1 eq.) in TFA (1.0 mL) and dichloromethane (5.0 mL) was stirred at 28° C. for 1 h. TLC (Petroleum ether/EtOAc=2/1) showed the starting material was consumed. The mixture was concentrated and the residue was adjusted to pH 8~9 with NH₃·H₂O (5 drops), then concentrated to give tert-butyl 3-((2-methoxypyridin-4-yl)methoxy)azetidine-1-carboxylate (95.0 mg, crude) as a yellow oil, which was used directly in next step without further purification.

Example 1-1

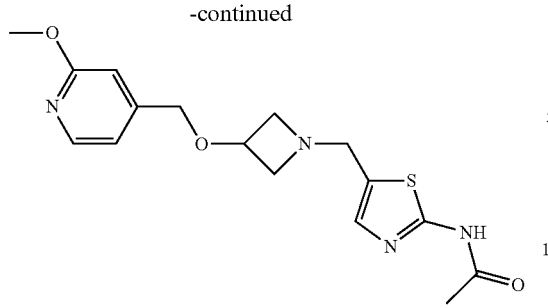

N-(5-((3-((2-methoxypyridin-4-yl)methoxy)azetidin-1-yl)methyl)thiazol-2-yl)acetamide: A mixture of 3-((3-methoxybenzyl)oxy)azetidine (95 mg, 489.11 μmol, 1 eq.) and N-(5-formylthiazol-2-yl)acetamide (125 mg, 733.67 umol, 1.5 eq.) in MeOH (10 mL) was stirred at 28° C. for 0.5 hr, then sodium cyanoborohydride (92 mg, 1.47 mmol, 3 eq.) was added, the mixture was stirred for another 2 hr. LCMS showed the starting material was consumed completely and desired compound was detected. The mixture was concentrated and the residue was purified by Prep-HPLC (Column: Xtimate C18 150*25 mm*5 um; Condition: water (10 mM NH$_4$HCO$_3$)-ACN; Begin B: 18; End B: 43; Gradient Time (min): 9; 100% B Hold Time (min): 2; FlowRate (ml/min): 25) to give N-(5-((3-((2-methoxypyridin-4-yl)methoxy)azetidin-1-yl)methyl)thiazol-2-yl)acetamide (120.6 mg, 70% yield) as a yellow solid. LCMS: [M+H] 349. $^1$HNMR: (500 MHz, CDCl$_3$) δ 11.63 (br s, 1H), 8.11 (d, J=5.5 Hz, 1H), 7.20 (s, 1H), 6.79-6.81 (m, 1H), 6.69 (s, 1H), 4.36-4.38 (m, 2H), 4.18-4.21 (m, 1H), 3.93 (s, 3H), 3.76 (s, 2H), 3.63-3.66 (m, 2H), 2.99-3.02 (m, 2H), 2.29 (s, 3H).

Example 1-2

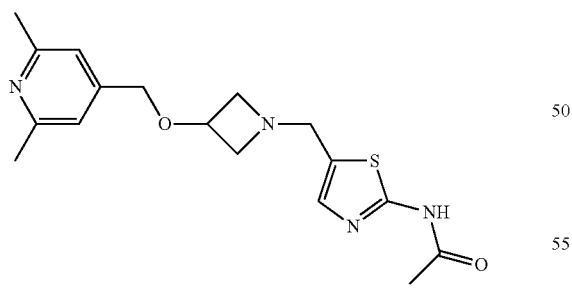

N-(5-((3-((2,6-dimethylpyridin-4-yl)methoxy)azetidin-1-yl)methyl)thiazol-2-yl)acetamide: The title compound was prepared in an analogous manner of that in scheme 1 from (2,6-dimethylpyridin-4-yl)methanol, tert-butyl 3-hydroxyazetidine-1-carboxylate and N-(5-formylthiazol-2-yl) acetamide. LCMS (ESI): [M+H] 347. $^1$HNMR: (400 MHz, CDCl$_3$) δ 12.37 (s, 1H), 7.19 (s, 1H), 6.47 (s, 2H), 4.08-4.10 (m, 2H), 3.73 (s, 2H), 3.39-3.43 (m, 2H), 3.10-3.13 (m, 2H), 2.88-2.89 (m, 1H), 2.45 (s, 6H), 2.29 (s, 3H).

Example 1-3

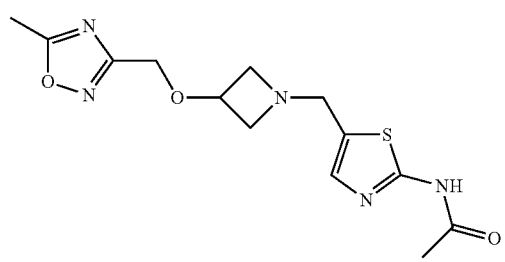 [SMILES: CC(=O)Nc1ncc(CN2CC(OCc3noc(C)n3)C2)s1]

N-(5-((3-((5-methyl-1,2,4-oxadiazol-3-yl)methoxy)azetidin-1-yl)methyl)thiazol-2-yl)acetamide: The title compound was prepared in an analogous manner of that in scheme 1 from (5-methyl-1,2,4-oxadiazol-3-yl)methanol, tert-butyl 3-hydroxyazetidine-1-carboxylate and N-(5-formylthiazol-2-yl)acetamide. LCMS (ESI): [M+H] 348. $^1$HNMR: (500 MHz, CD$_3$OD) δ 7.27 (s, 1H), 6.55 (s, 1H), 4.46 (d, J=6.4 Hz, 2H), 3.81 (s, 2H), 3.47 (t, J=8.0 Hz, 2H), 3.19 (t, J=7.6 Hz, 2H), 2.89-2.96 (m, 1H), 2.51 (s, 3H), 2.38 (s, 3H), 2.19 (s, 3H).

Scheme 2

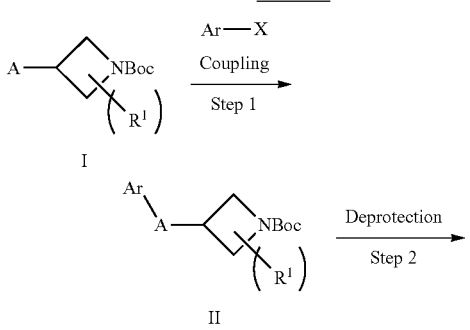

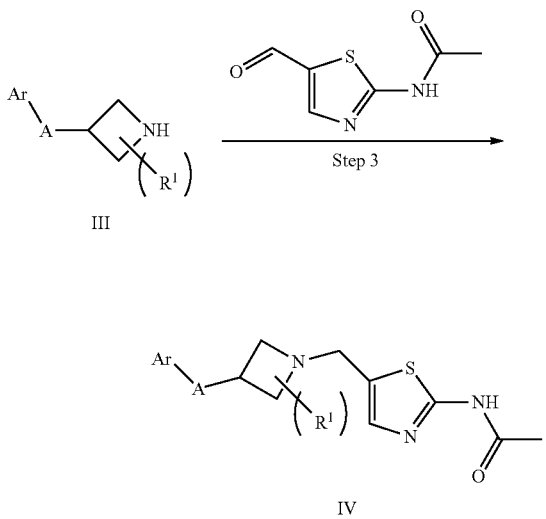

A = O, N, CH$_2$ R$^1$ = H, Me

Intermediate 4

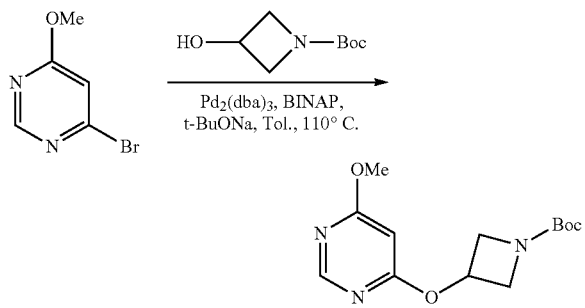

tert-butyl 3-((6-methoxypyrimidin-4-yl)oxy)azetidine-1-carboxylate: To a solution of 4-bromo-6-methoxypyrimidine (1.0 g, 6.92 mmol, 1 eq.) and tert-butyl 3-hydroxyazetidine-1-carboxylate (1.2 g, 6.92 mmol, 1 eq.) in toluene (20 mL) was added Pd$_2$(dba)$_3$ (317 mg, 346 ummol, 0.1 eq.), BINAP (215 mg, 346 ummol, 0.2 eq.) and sodium tert-butoxide (1.3 g, 13.83 mmol, 2 eq.). The reaction was stirred at 110° C. for 1 hour. LCMS showed the desired product was detected. The reaction was concentrated to give a crude product, which was purified by column chromatography (petroleum ether: ethyl acetate=3:1) to give compound 3 (450 mg, 23% yield) as yellow oil. LCMS (ESI): [M+H] 282. $^1$HNMR: (500 MHz, CDCl$_3$) δ 8.38 (s, 1H), 6.08 (s, 1H), 5.30-5.33 (m, 1H), 4.29-4.32 (m, 2H), 3.95-4.12 (m, 2H), 3.95 (s, 3H), 1.44 (s, 9H).

Intermediate 5

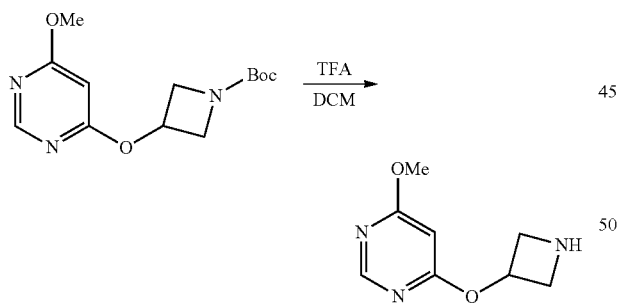

4-(azetidin-3-yloxy)-6-methoxypyrimidine: To a solution of tert-butyl 3-((6-methoxypyrimidin-4-yl)oxy)azetidine-1-carboxylate (450 mg, 1.60 mmol) in DCM (10 mL) was added TFA (1 mL). The mixture was stirred at 30° C. for 2 hours. TLC (Petroleum ether: Ethyl acetate=1:1) showed the start material was consumed completely. The reaction was concentrated to give a product. H$_2$O (2 mL) was added and the aqueous layer extracted with CH$_2$Cl$_2$ (3×4 mL). The aqueous phase was adjusted to pH 8 by adding NH$_3$·H$_2$O. Then concentrated to give 4-(azetidin-3-yloxy)-6-methoxypyrimidine (200 mg, 69% yield), which was used for the next step without purification.

Example 2-1

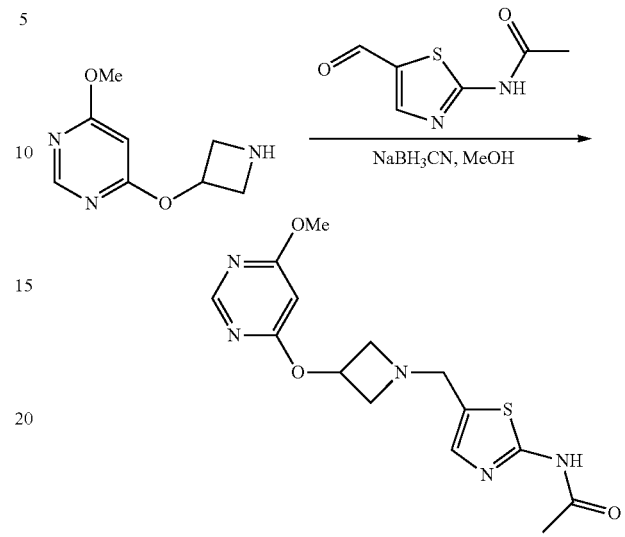

N-(5-((3-((6-methoxypyrimidin-4-yl)oxy)azetidin-1-yl)methyl)thiazol-2-yl)acetamide: To a solution of 4-(azetidin-3-yloxy)-6-methoxypyrimidine (220 mg, 1.21 mmol, 1 eq.) and N-(5-formylthiazol-2-yl)acetamide (206 mg, 1.21 mmol, 1 eq.) in MeOH (15 mL) was stirred at 50° C. for 0.5 hour. Sodium cyanoborohydride (228 mg, 3.63 mmol, 3 eq.) was added to the mixture. The reaction was stirred at 50° C. for 12 hours. LCMS showed the desired product was detected. The reaction was concentrated to give a crude product, which was purified by pre-HPLC (Column: Waters Xbridge Prep OBD C18 150*30 5u, Condition: water (0.04% NH$_3$H$_2$O+10 mM NH$_4$HCO$_3$)-ACN, Begin B: 15; End B: 45, Gradient Time (min): 10, 100% B Hold Time (min): 2, Flow Rate (ml/min): 25) to give N-(5-((3-((6-methoxypyrimidin-4-yl)oxy)azetidin-1-yl)methyl)thiazol-2-yl)acetamide (90 mg, 22% yield) as white solid. LCMS (ESI): [M+H] 335.9. $^1$HNMR: (400 MHz, DMSO) δ: 11.86 (br s, 1H), 8.41 (s, 1H), 7.24 (s, 1H), 6.24 (s, 1H), 5.11-5.17 (m, 1H), 3.85 (s, 3H), 3.71 (s, 2H), 3.61-3.65 (m, 2H), 3.03-3.07 (m, 2H), 2.08 (s. 3H).

Example 2-2

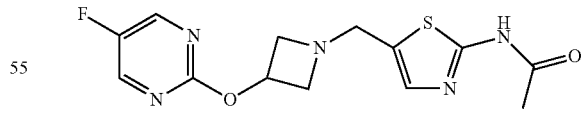

N-(5-43-((5-fluoropyrimidin-2-yl)oxy)azetidin-1-yl)methyl)thiazol-2-yl)acetamide: The title compound was prepared in an analogous manner of that in scheme 2 from 2-bromo-5-fluoropyrimidine, tert-butyl 3-hydroxyazetidine-1-carboxylate and N-(5-formylthiazol-2-yl)acetamide. LCMS (ESI): [M+H] 324. $^1$HNMR: (400 MHz, CDCl$_3$) δ 11.64 (br s, 1H), 8.35 (s, 2H), 7.22 (s, 1H), 5.17-5.24 (m, 1H), 3.88 (dd, J=6.0, 8.8 Hz, 2H), 3.82 (s, 2H), 3.19 (dd, J=6.0, 9.2 Hz, 2H), 2.30 (s, 3H).

Example 2-3

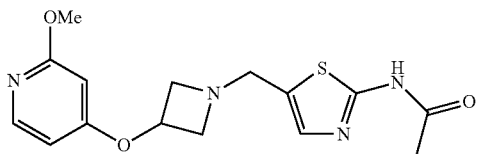 [SMILES: COc1cc(OC2CN(Cc3cnc(NC(C)=O)s3)C2)ccn1]

N-(5-((3-((2-methoxypyridin-4-yl)oxy)azetidin-1-yl)methyl)thiazol-2-yl)acetamide: The title compound was prepared in an analogous manner of that in scheme 2 from 4-bromo-2-methoxypyridine, tert-butyl 3-hydroxyazetidine-1-carboxylate and N-(5-formylthiazol-2-yl)acetamide. LCMS (ESI): [M+H] 335. $^1$HNMR: (400 MHz, CDCl$_3$) δ: 10.87 (s, 1H), 7.96 (d, J=6.0 Hz, 1H), 7.22 (s, 1H), 6.37 (d, J=6.0 Hz, 1H), 5.99 (s, 1H), 4.77-4.83 (m, 1H), 3.90 (s, 3H), 3.82-3.85 (m, 4H), 3.16-3.20 (m, 2H), 2.29 (s, 3H).

Example 2-4

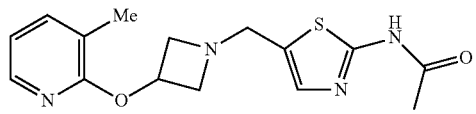 [SMILES: CC(=O)Nc1ncc(CN2CC(Oc3ncccc3C)C2)s1]

N-(5-((3-((3-methylpyridin-2-yl)oxy)azetidin-1-yl)methyl)thiazol-2-yl)acetamide: The title compound was prepared in an analogous manner of that in scheme 2 from 2-chloro-3-methylpyridine, tert-butyl 3-hydroxyazetidine-1-carboxylate and N-(5-formylthiazol-2-yl)acetamide. LCMS (ESI): [M+H] 319. $^1$HNMR: (400 MHz, D$_2$O) =8.25 (d, J=6.0 Hz, 1H), 8.19 (d, J=7.2 Hz, 1H), 7.57 (s, 1H), 7.43 (t, J=6.8 Hz, 1H), 5.72-5.79 (m, 1H), 5.18-5.42 (m, 1H), 4.81-4.85 (m, 1H), 4.52-4.61 (m, 2H), 3.60-3.71 (m, 2H), 2.35 (s, 3H), 2.26 (s, 3H).

Example 2-5

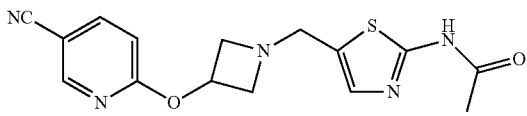 [SMILES: CC(=O)Nc1ncc(CN2CC(Oc3ccc(C#N)cn3)C2)s1]

N-(5-((3-((5-cyanopyridin-2-yl)oxy)azetidin-1-yl)methyl)thiazol-2-yl)acetamide: The title compound was prepared in an analogous manner of that in scheme 2 from 6-chloronicotinonitrile, tert-butyl 3-hydroxyazetidine-1-carboxylate and N-(5-formylthiazol-2-yl)acetamide. LCMS (ESI): [M+H] 323. $^1$HNMR: (400 MHz, CDCl$_3$) δ 10.69 (s, 1H), 8.42 (s, 1H), 7.79 (d, J=8.8 Hz, 1H), 7.22 (s, 1H), 6.83 (d, J=8.8 Hz, 1H), 5.28-5.36 (m, 1H), 3.82-3.85 (m, 4H), 3.20-3.23 (m, 2H), 2.29 (s, 3H).

Example 2-6

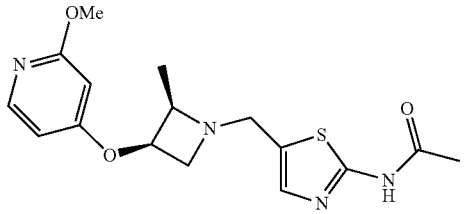 [SMILES: COc1cc(O[C@@H]2CN(Cc3cnc(NC(C)=O)s3)[C@@H]2C)ccn1]

N-(5-(((2R,3R)-3-((2-methoxypyridin-4-yl)oxy)-2-methylazetidin-1-yl)methyl)thiazol-2-yl)acetamide: The title compound was prepared in an analogous manner of that in scheme 2 from 4-bromo-2-methoxypyridine, tert-butyl 3-hydroxy-2-methylazetidine-1-carboxylate and N-(5-formylthiazol-2-yl)acetamide. The diastereomers were separated by pre-HPLC (Mobile phase: water (0.05% ammonia hydroxide)-ACN; Column: water xbrige prep OBD C$_{18}$ 150*30 mm*5 um; Detection. wavelength: 220 nm. LCMS (ESI): [M+H] 349. $^1$HNMR: (400 MHz, CD$_3$OD) δ 7.91 (d, J=6.0 Hz, 1H), 7.28 (s, 1H), 6.54 (dd, J=6.0 Hz, 2.4 Hz, 1H), 6.17 (s, 1H), 4.92-5.00 (m, 1H), 3.91-3.92 (m, 1H), 3.80 (s, 3H), 3.76-3.78 (m, 2H), 3.38-3.44 (m, 2H), 2.18 (s, 3H), 1.10 (s, 3H).

Example 2-7

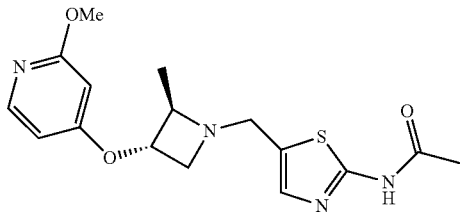 [SMILES: COc1cc(O[C@H]2CN(Cc3cnc(NC(C)=O)s3)[C@@H]2C)ccn1]

N-(5-(((2R,3S)-3-((2-methoxypyridin-4-yl)oxy)-2-methylazetidin-1-yl)methyl)thiazol-2-yl)acetamide: The title compound was prepared in an analogous manner of that in scheme 2 from 4-bromo-2-methoxypyridine, tert-butyl 3-hydroxy-2-methylazetidine-1-carboxylate and N-(5-formylthiazol-2-yl)acetamide. The diastereomers were separated by pre-HPLC (Mobile phase: water (0.05% ammonia hydroxide)-ACN; Column: water xbrige prep OBD C$_{18}$ 150*30 mm*5 um; Detection. wavelength: 220 nm. LCMS (ESI): [M+H] 349. $^1$HNMR: (400 MHz, CD$_3$OD) δ 7.91 (d, J=6.0 Hz, 1H), 7.28 (s, 1H), 6.50 (dd, J=6.0 Hz, 2.5 Hz, 1H), 6.18 (s, 1H), 4.44-4.45 (m, 1H), 3.95-3.96 (m, 1H), 3.83-3.85 (m, 4H), 3.77-3.80 (m, 1H), 3.38-3.41 (m, 1H), 2.86-2.89 (m, 1H), 2.20 (s, 3H), 1.24 (s, 3H).

Example 2-8

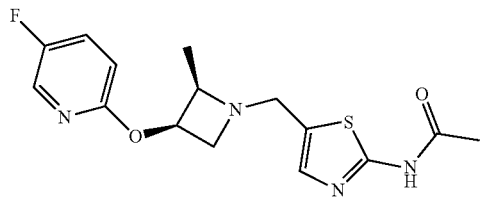 [SMILES: CC(=O)Nc1ncc(CN2C[C@@H](Oc3ccc(F)cn3)[C@H]2C)s1]

N-(5-(((2R,3R)-3-((5-fluoropyridin-2-yl)oxy)-2-methyl-azetidin-1-yl)methyl)thiazol-2-yl)acetamide: The title compound was prepared in an analogous manner of that in scheme 2 from 2-bromo-5-fluoropyridine, tert-butyl 3-hydroxy-2-methylazetidine-1-carboxylate and N-(5-formylthiazol-2-yl)acetamide. The diastereomers were separated by Prep-HPLC (Column: Xtimate C18 150*25 mm*5 um; Condition: water (10 mM NH$_4$HCO$_3$)-ACN; Begin B: 36; End B: 66; Gradient Time (min): 10; 100% B Hold Time (min): 2; FlowRate (ml/min): 25). LCMS (ESI): [M+H] 337. $^1$HNMR: (400 MHz, CD$_3$OD) δ 7.96 (d, J=2.8 Hz, 1H), 7.47-7.53 (m, 1H), 7.29 (s, 1H), 6.77-6.80 (m, 1H), 4.75-4.80 (m, 1H), 3.93-3.97 (m, 1H), 3.78-3.86 (m, 2H), 3.34-3.38 (m, 1H), 2.91-2.95 (m, 1H), 2.20 (s, 3H), 1.26 (d, J=6.0 Hz, 3H).

Example 2-9

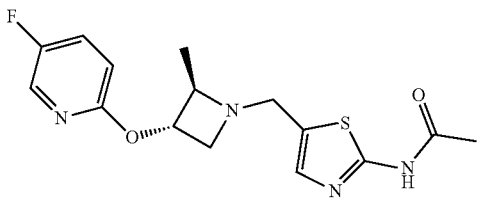 [SMILES: CC(=O)Nc1ncc(CN2C[C@H](Oc3ccc(F)cn3)[C@H]2C)s1]

N-(5-(((2R,3S)-3-((5-fluoropyridin-2-yl)oxy)-2-methyl-azetidin-1-yl)methyl)thiazol-2-yl)acetamide: The title compound was prepared in an analogous manner of that in scheme 2 from 2-bromo-5-fluoropyridine, tert-butyl 3-hydroxy-2-methylazetidine-1-carboxylate and N-(5-formylthiazol-2-yl)acetamide. The diastereomers were separated by Prep-HPLC (Column: Xtimate C18 150*25 mm*5 um; Condition: water (10 mM NH$_4$HCO$_3$)-ACN; Begin B: 36; End B: 66; Gradient Time (min): 10; 100% B Hold Time (min): 2; FlowRate (ml/min): 25). LCMS (ESI): [M+H] 337. $^1$HNMR: (400 MHz, CD$_3$OD) δ 7.94 (d, J=2.8 Hz, 1H), 7.49-7.54 (m, 1H), 7.29 (s, 1H), 6.86-6.89 (m, 1H), 5.30-5.34 (m, 1H), 3.88-3.92 (m, 1H), 3.70-3.81 (m, 2H), 3.43 (d, J=4.0 Hz, 2H), 2.19 (s, 3H), 1.07 (d, J=6.8 Hz, 3H).

Example 2-10

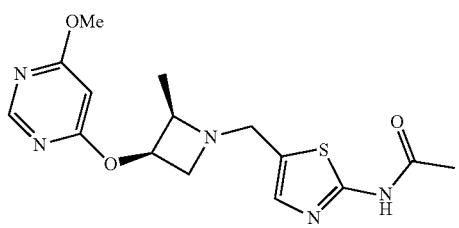 [SMILES: COc1cc(O[C@@H]2CN(Cc3cnc(NC(C)=O)s3)[C@@H]2C)ncn1]

N-(5-(((2R,3R)-3-((6-methoxypyrimidin-4-yl)oxy)-2-methylazetidin-1-yl)methyl)thiazol-2-yl)acetamide: The title compound was prepared in an analogous manner of that in scheme 2 from 4-chloro-6-methoxypyrimidine, tert-butyl 3-hydroxy-2-methylazetidine-1-carboxylate and N-(5-formylthiazol-2-yl)acetamide. LCMS (ESI): [M+H] 349. $^1$HNMR: (400 MHz, CD$_3$OD) δ 8.09 (s, 1H), 7.26 (s, 1H), 5.86 (s, 1H), 3.85-3.89 (m, 5H), 3.71-3.74 (m, 1H), 3.60-3.63 (m, 1H), 3.41-3.43 (m, 1H), 3.26-3.39 (m, 1H), 2.19 (s, 3H), 0.97 (d, J=6.4 Hz, 3H).

Example 2-11

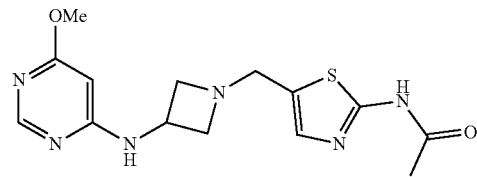 [SMILES: COc1cc(NC2CN(Cc3cnc(NC(C)=O)s3)C2)ncn1]

N-(5-((3-((5-cyanopyridin-2-yl)oxy)azetidin-1-yl)methyl)thiazol-2-yl)acetamide: The title compound was prepared in an analogous manner of that in scheme 2 from 4-bromo-6-methoxypyrimidine, tert-butyl 3-aminoazetidine-1-carboxylate and N-(5-formylthiazol-2-yl)acetamide. LCMS (ESI): [M+H] 335. $^1$HNMR: (500 MHz, CDCl$_3$) δ 11.86 (s, 1H), 8.27 (s, 1H), 7.22 (s, 1H), 6.86 (s, 1H), 5.52 (s, 1H), 4.18-4.19 (m, 1H), 3.91 (s, 3H), 3.79 (s, 2H), 3.71 (t, J=6.5 Hz, 2H), 3.05-3.08 (m, 2H), 2.29 (s, 3H).

Example 2-12

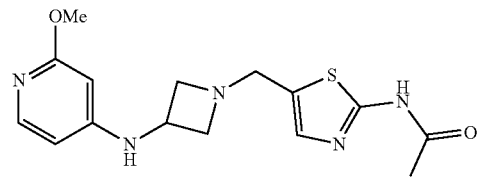

N-(5-((3-((2-methoxypyridin-4-yl)amino)azetidin-1-yl)methyl)thiazol-2-yl)acetamide: The title compound was prepared in an analogous manner of that in scheme 2 from 4-bromo-2-methoxypyridine, tert-butyl 3-aminoazetidine-1-carboxylate, and N-(5-formylthiazol-2-yl)acetamide. LCMS (ESI): [M+H] 335. $^1$HNMR: (500 MHz, CDCl$_3$) δ 11.86 (s, 1H), 8.27 (s, 1H), 7.22 (s, 1H), 6.86 (s, 1H), 5.52 (s, 1H), 4.18-4.19 (m, 1H), 3.91 (s, 3H), 3.79 (s, 2H), 3.71 (t, J=6.5 Hz, 2H), 3.05-3.08 (m, 2H), 2.29 (s, 3H).

Example 2-13

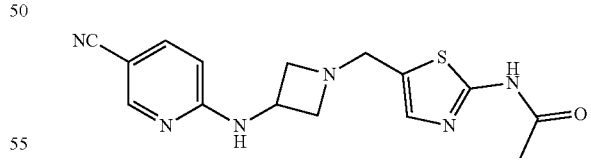

N-(5-((3-((5-cyanopyridin-2-yl)amino)azetidin-1-yl)methyl)thiazol-2-yl)acetamide: The title compound was prepared in an analogous manner of that in scheme 2 from 6-chloronicotinonitrile, tert-butyl 3-aminoazetidine-1-carboxylate, and N-(5-formylthiazol-2-yl)acetamide. LCMS (ESI): [M+H] 329. $^1$HNMR: (500 MHz, CD$_3$OD) δ 11.97 (br s, 1H), 8.40 (s, 1H), 8.06 (d, J=6.5 Hz, 1H), 7.71 (d, J=8.0 Hz, 1H), 6.55 (d, J=9.0 Hz, 1H), 4.43-4.44 (m, 1H), 3.71 (s, 2H), 3.57-3.59 (m, 2H), 2.92-2.95 (m, 2H), 2.14 (s, 3H).

Intermediate 6

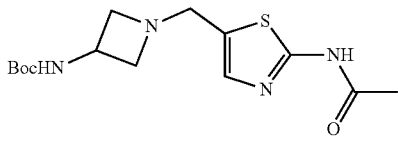 [SMILES: CC(=O)Nc1ncc(CN2CC(NC(=O)OC(C)(C)C)C2)s1]

tert-butyl (1-((2-acetamidothiazol-5-yl)methyl)azetidin-3-yl)carbamate: A solution of tert-butyl azetidin-3-ylcarbamate (5.0 g, 29.03 mmol, 1 eq.) and N-(5-formylthiazol-2-yl)acetamide (4.9 g, 29.03 mmol, 1 eq.) in MeOH (100 mL) was stirred at 50° C. for 0.5 h then sodium cyanoborohydride (5.5 g, 87.09 mmol, 3 eq.) was added to the mixture. The reaction was stirred at 50° C. for 1 h. LCMS showed the desired product was detected. The reaction was quenched with H$_2$O (5 mL), which was purified by column chromatography (Ethyl acetate) to give tert-butyl (1-((2-acetamidothiazol-5-yl)methyl)azetidin-3-yl)carbamate (7 g, 74% yield) as brown solid. LCMS (ESI): [M+H] 327. $^1$HNMR: (400 MHz, CD$_3$OD) δ 7.27 (s, 1H), 4.18-4.23 (m, 1H), 3.84 (s, 2H), 3.68-3.69 (m, 2H), 3.08-3.11 (m, 2H), 2.19 (s, 3H), 1.41 (s, 9H).

Intermediate 7

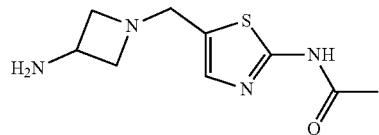

N-(5-((3-aminoazetidin-1-yl)methyl)thiazol-2-yl)acetamide: To a solution of tert-butyl (1-((2-acetamidothiazol-5-yl)methyl)azetidin-3-yl)carbamate (2 g, 6.13 mmol, 1 eq.) in DCM (30 mL) was added TFA (5 mL). The mixture was stirred at 50° C. for 2 h. TLC (Ethyl acatate) showed the starting material was consumed completely. The reaction was concentrated to give a product. To the mixture was added H$_2$O (8 mL) and the aqueous layer was extracted with DCM (4 mL). The aqueous layer was adjusted to pH 8 by adding NH$_3$·H$_2$O. Then concentrated to give the residue, which was purified by prep-HPLC (Column: Waters Xbridge Prep OBD C18 100*19 5u, Condition: water (0.04% NH$_3$H$_2$O+10 mM NH4HCO3)-ACN, Begin B: 0; End B: 30, Gradient Time (min): 10, 100% B Hold Time (min): 2, FlowRate (ml/min): 25) to give N-(5-((3-aminoazetidin-1-yl)methyl)thiazol-2-yl)acetamide (300 mg, 22% yield) as white solid. LCMS (ESI): [M+H] 227. $^1$HNMR: (400 MHz, CD$_3$OD) δ 7.24 (s, 1H), 3.76 (s, 2H), 3.52-3.62 (m, 3H), 2.85-2.89 (m, 2H), 2.19 (s, 3H).

Example 2-14

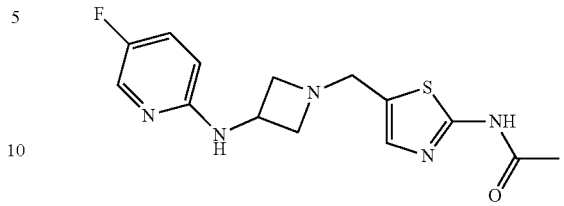

N-(5-((3-((5-fluoropyridin-2-yl)amino)azetidin-1-yl)methyl)thiazol-2-yl)acetamide: To a solution of N-(5-((3-aminoazetidin-1-yl)methyl)thiazol-2-yl)acetamide (150 mg, 662.84 umol) and 2-chloro-5-fluoropyridine (110 mg, 835.18 umol, 84.51 uL) in DMF (10 mL) was added Pd$_2$(dba)$_3$ (60 mg, 66.28 umol, 0.1 eq.), sodium tert-butoxide (127 mg, 1.33 mmol, 2 eq.) and XPhos (63 mg, 132.57 umol, 0.2 eq.). The reaction was degassed with N$_2$ three times and stirred at 110° C. for 3 h. LCMS showed the desired product was detected. The reaction was quenched with H$_2$O (10 mL), and extracted with ethyl acetate (20 mL). The combined organic layer was washed with H$_2$O (20 mL) and brine (20 mL), dried over Na$_2$SO$_4$, filtered, the filtrate was concentrated to give a crude product, which was purified by prep-HPLC ((Column: Waters Xbridge Prep OBD C18 100*19 5u, Condition: water (0.04% NH$_3$H$_2$O+10 mM NH$_4$HCO$_3$)-ACN, Begin B: 11; End B: 41, Gradient Time (min): 10, 100% B Hold Time (min): 2, Flow Rate (ml/min): 25)) to give N-(5-((3-((5-fluoropyridin-2-yl)amino)azetidin-1-yl)methyl)thiazol-2-yl)acetamide (42.90 mg, 133.49 umol, 20% yield) as light yellow solid.

Example 2-15

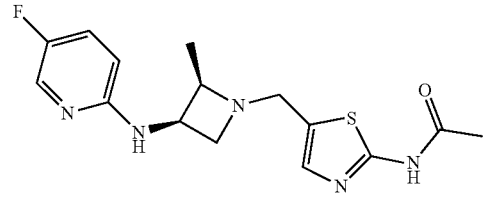 [SMILES: CC(=O)Nc1ncc(CN2C[C@@H](Nc3ccc(F)cn3)[C@H]2C)s1]

N-(5-(((2R,3R)-3-((5-fluoropyridin-2-yl)amino)-2-methylazetidin-1-yl)methyl)thiazol-2-yl)acetamide: The title compound was prepared in an analogous manner of that in scheme 3 from 2-chloro-5-fluoropyridine, tert-butyl 3-amino-2-methylazetidine-1-carboxylate and N-(5-formylthiazol-2-yl)acetamide. LCMS (ESI): [M+H] 335.9. $^1$HNMR: (500 MHz, CD$_3$OD) δ 7.80 (d, J=3.0 Hz, 1H), 7.29-7.33 (m, 2H), 6.61-6.63 (m, 1H), 4.44-4.47 (m, 1H), 3.91 (d, J=13.5 Hz, 1H), 3.77 (d, J=13.5 Hz, 1H), 3.64-3.70 (m, 1H), 3.46 (t, J=8.0 Hz, 1H), 3.27-3.30 (m, 1H), 2.22 (s, 3H), 1.00 (d, J=6.5 Hz, 3H).

Example 2-16

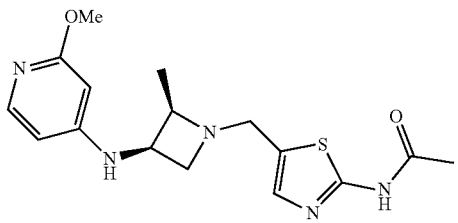 [SMILES: COc1cc(N[C@@H]2CN(Cc3cnc(NC(C)=O)s3)[C@@H]2C)ccn1]

N-(5-(((2R,3R)-3-((2-methoxypyridin-4-yl)amino)-2-methylazetidin-1-yl)methyl)thiazol-2-yl)acetamide: The title compound was prepared in an analogous manner of that in scheme 2 from 4-bromo-2-methoxypyridine, tert-butyl 3-amino-2-methylazetidine-1-carboxylate and N-(5-formylthiazol-2-yl)acetamide. The diastereomers were separated by Prep-HPLC (Column: Xtimate C18 150*25 mm*5 um; Condition: water (10 mM $NH_4HCO_3$)-ACN; Begin B: 11; End B: 41; Gradient Time (min): 10; 100% B Hold Time (min): 2; Flow Rate (ml/min): 25) LCMS (ESI): [M+H] 348. $^1$HNMR: (400 MHz, $CDCl_3$) δ11.54 (s, 1H), 7.78 (d, J=6.4 Hz, 1H), 7.20 (s, 1H), 6.13-6.15 (m, 1H), 5.75 (s, 1H), 4.74 (d, J=8.4 Hz, 1H), 4.04-4.06 (m, 1H), 3.83-3.87 (m, 4H), 3.63-3.67 (m, 1H), 3.54-3.56 (m, 1H), 3.29-3.31 (m, 1H), 3.21-3.23 (m, 1H), 2.30 (s, 3H), 1.03 (d, J=6.4 Hz, 3H).

Example 2-17

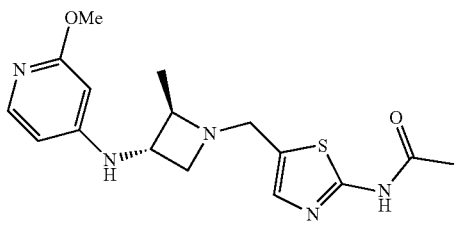 [SMILES: COc1cc(N[C@H]2CN(Cc3cnc(NC(C)=O)s3)[C@@H]2C)ccn1]

N-(5-(((2R,3S)-3-((2-methoxypyridin-4-yl)amino)-2-methylazetidin-1-yl)methyl)thiazol-2-yl)acetamide: The title compound was prepared in an analogous manner of that in scheme 2 from 4-bromo-2-methoxypyridine, tert-butyl 3-amino-2-methylazetidine-1-carboxylate and N-(5-formylthiazol-2-yl)acetamide. The diastereomers were separated by Prep-HPLC (Column: Xtimate C18 150*25 mm*5 um; Condition: water (10 mM $NH_4HCO_3$)-ACN; Begin B: 11; End B: 41; Gradient Time (min): 10; 100% Hold Time (min): 2; Flow Rate (ml/min): 25) LCMS (ESI): [M+H] 347.9. $^1$HNMR: (400 MHz, $CDCl_3$) δ12.10 (s, 1H), 7.78 (d, J=6.0 Hz, 1H), 7.20 (s, 1H), 6.09 (d, J=5.6 Hz, 1H), 5.79 (s, 1H), 4.26 (d, J=7.2 Hz, 1H), 3.82-3.86 (m, 4H), 3.80-3.83 (m, 1H), 3.65-3.71 (m, 2H), 2.99-3.02 (m, 1H), 2.59-2.62 (m, 1H), 2.30 (s, 3H), 1.27 (d, J=5.6 Hz, 3H).

Example 2-18

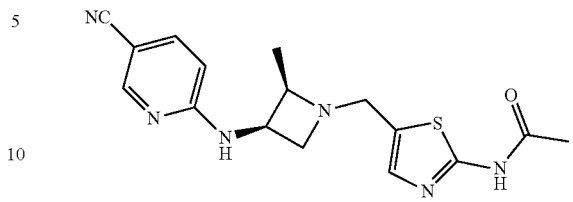

N-(5-(((2R,3R)-3-((5-cyanopyridin-2-yl)amino)-2-methylazetidin-1-yl)methyl)thiazol-2-yl)acetamide: The title compound was prepared in an analogous manner of that in scheme 2 from 6-chloronicotinonitrile, tert-butyl 3-amino-2-methylazetidine-1-carboxylate and N-(5-formylthiazol-2-yl)acetamide. The diastereomers were separated at intermediate 1 by Prep-HPLC (Column: Xtimate C18 150*25 mm*5 um; Condition: water (10 mM $NH_4HCO_3$)-ACN; Begin B: 11; End B: 41; Gradient Time (min): 10; 100% B Hold Time (min): 2; Flow Rate (ml/min): 25) LCMS (ESI): [M+H] 342.9. $^1$HNMR: (400 MHz, $CDCl_3$) δ: 11.01 (s, 1H), 8.33 (s, 1H), 7.55 (d, J=5.2 Hz, 1H), 7.23 (s, 1H), 6.41 (d, J=8.4 Hz, 1H), 5.84 (br s, 1H), 4.52-4.53 (m, 1H), 3.85-3.89 (m, 1H), 3.58-3.59 (m, 1H), 3.52-3.56 (m, 1H), 3.31-3.35 (m, 1H), 3.24-3.26 (m, 1H), 2.29 (s, 3H), 1.01 (d, J=6.0 Hz, 3H).

Example 2-19

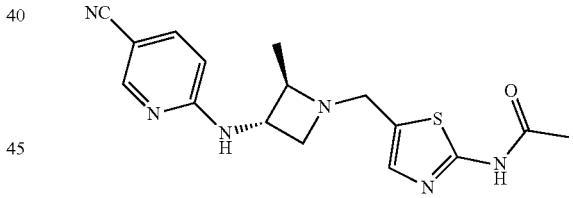

N-(5-(((2R,3S)-3-((5-cyanopyridin-2-yl)amino)-2-methylazetidin-1-yl)methyl)thiazol-2-yl)acetamide: The title compound was prepared in an analogous manner of that in scheme 2 from 6-chloronicotinonitrile, tert-butyl 3-amino-2-methylazetidine-1-carboxylate and N-(5-formylthiazol-2-yl)acetamide. The diastereomers were separated at intermediate 1 by Prep-HPLC (Column: Xtimate C18 150*25 mm*5 um; Condition: water (10 mM $NH_4HCO_3$)-ACN; Begin B: 11; End B: 41; Gradient Time (min): 10; 100% B Hold Time (min): 2; Flow Rate (ml/min): 25) LCMS (ESI): [M+H] 342.9. $^1$HNMR: (400 MHz, $CDCl_3$) δ: 10.86 (br s, 1H), 8.34 (s, 1H), 7.58-7.60 (m, 1H), 7.21-7.22 (m, 1H), 6.34-6.36 (m, 1H), 5.42 (br s, 1H), 3.68-4.00 (m, 4H), 3.06-3.07 (m, 1H), 2.67-2.68 (m, 1H), 2.28 (s, 3H), 1.27 (d, J=6.0 Hz, 3H).

Example 2-20

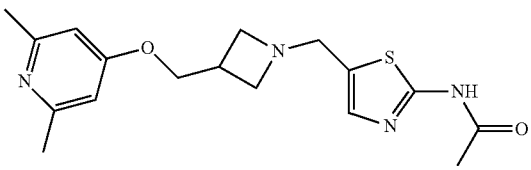 [SMILES: CC(=O)Nc1ncc(CN2CC(COc3cc(C)nc(C)c3)C2)s1]

N-(5-((3-(((2,6-dimethylpyridin-4-yl)oxy)methyl)azetidin-1-yl)methyl)thiazol-2-yl)acetamide: The title compound was prepared in an analogous manner of that in scheme 2 from 4-bromo-2,6-dimethylpyridine, tert-butyl 3-(hydroxymethyl)azetidine-1-carboxylate, and N-(5-formylthiazol-2-yl)acetamide. LCMS (ESI): [M+H] 347. $^1$HNMR: (400 MHz, CD$_3$OD) δ 11.45 (s, 1H), 7.20 (s, 1H), 6.90 (s, 2H), 4.35 (s, 2H), 4.19-4.24 (m, 1H), 3.77 (s, 2H), 3.63-3.67 (m, 2H), 3.00-3.04 (m, 2H), 2.51 (s, 6H), 2.29 (s, 3H).

Example 2-21

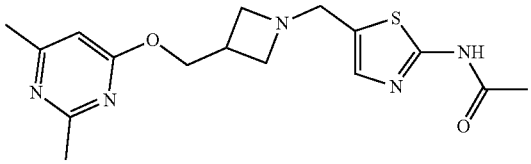 [SMILES: CC(=O)Nc1ncc(CN2CC(COc3cc(C)nc(C)n3)C2)s1]

N-(5-((3-(((2,6-dimethylpyrimidin-4-yl)oxy)methyl)azetidin-1-yl)methyl)thiazol-2-yl)acetamide: The title compound was prepared in an analogous manner of that in scheme 2 from 4-chloro-2,6-dimethylpyrimidine, tert-butyl 3-(hydroxymethyl)azetidine-1-carboxylate, and N-(5-formylthiazol-2-yl)acetamide. LCMS (ESI): [M+H] 348. $^1$HNMR: (400 MHz, CD$_3$OD) δ 7.27 (s, 1H), 6.55 (s, 1H), 4.46 (d, J=6.4 Hz, 2H), 3.81 (s, 2H), 3.47 (t, J=8.0 Hz, 2H), 3.19 (t, J=8.0 Hz, 2H), 2.89-2.96 (m, 1H), 2.51 (s, 3H), 2.38 (s, 3H), 2.19 (s, 3H).

Example 2-22

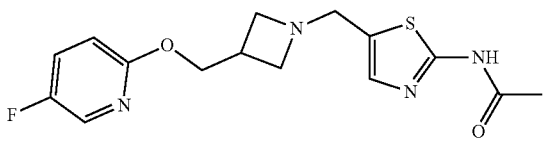 [SMILES: CC(=O)Nc1ncc(CN2CC(COc3ccc(F)cn3)C2)s1]

N-(5-((3-(((5-fluoropyridin-2-yl)oxy)methyl)azetidin-1-yl)methyl)thiazol-2-yl)acetamide: The title compound was prepared in an analogous manner of that in scheme 2 from 2-chloro-5-fluoropyridine, tert-butyl 3-(hydroxymethyl)azetidine-1-carboxylate, and N-(5-formylthiazol-2-yl)acetamide. LCMS (ESI): [M+H] 337. $^1$HNMR: (400 MHz, CDCl$_3$) δ 10.96-11.03 (m, 1H), 7.96 (d, J=2.4 Hz, 1H), 7.20-7.35 (m, 2H), 6.67-6.71 (m, 1H), 4.36 (d, J=6.4 Hz, 2H), 3.74 (s, 2H), 3.45-3.48 (m, 2H), 3.11-3.14 (m, 2H), 2.90-2.95 (m, 1H), 2.30 (s, 3H).

Example 2-23

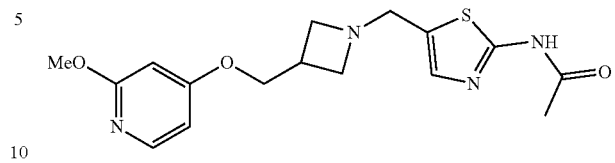

N-(5-((3-(((2-methoxypyridin-4-yl)oxy)methyl)azetidin-1-yl)methyl)thiazol-2-yl)acetamide: The title compound was prepared in an analogous manner of that in scheme 2 from 4-bromo-2-methoxypyridine, tert-butyl 3-(hydroxymethyl)azetidine-1-carboxylate, and N-(5-formylthiazol-2-yl)acetamide. LCMS (ESI): [M+H] 349. $^1$HNMR: (400 MHz, CDCl$_3$) δ 11.86 (br s, 1H), 7.96 (d, J=6.0 Hz, 1H), 7.20 (s, 1H), 6.46 (d, J=6.0 Hz, 1H), 6.17 (d, J=2.0 Hz, 1H), 4.09 (d, J=7.0 Hz, 2H), 3.91 (s, 3H), 3.74 (s, 2H), 3.43 (t, J=7.5 Hz, 2H), 3.11-3.14 (m, 2H), 2.88-2.92 (m, 1H), 2.30 (s, 3H).

Example 2-24

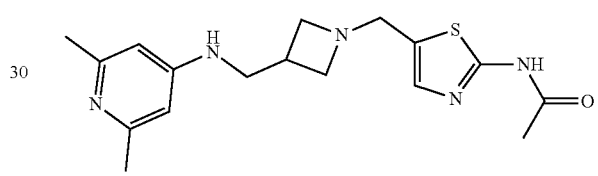

N-(5-((3-(((2,6-dimethylpyridin-4-yl)amino)methyl)azetidin-1-yl)methyl)thiazol-2-yl)acetamide: The title compound was prepared in an analogous manner of that in scheme 2 from 4-bromo-2,6-dimethylpyridine, tert-butyl 3-(aminomethyl)azetidine-1-carboxylate, and N-(5-formylthiazol-2-yl)acetamide. LCMS (ESI): [M+H] 346. $^1$HNMR: (400 MHz, CD$_3$OD) δ 7.26 (s, 1H), 6.36 (s, 2H), 3.77 (s, 2H), 3.37-3.45 (m, 4H), 3.05-3.08 (m, 2H), 2.73-2.77 (m, 1H), 2.35 (s, 6H), 2.20 (s, 3H).

Example 2-25

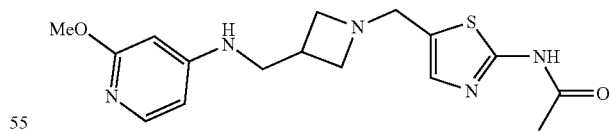

N-(5-((3-(((2-methoxypyridin-4-yl)amino)methyl)azetidin-1-yl)methyl)thiazol-2-yl)acetamide: The title compound was prepared in an analogous manner of that in scheme 2 from 4-bromo-2-methoxypyridine, tert-butyl 3-(aminomethyl)azetidine-1-carboxylate, and N-(5-formylthiazol-2-yl)acetamide. LCMS (ESI): [M+H] 348. $^1$HNMR: (400 MHz, CDCl$_3$) δ 11.82 (br s, 1H), 7.78 (d, J=6.0 Hz, 1H), 7.18 (s, 1H), 6.16-6.14 (m, 1H), 5.81 (s, 1H), 4.70-4.73 (m, 1H), 3.87 (s, 3H), 3.71 (s, 2H), 3.33-3.37 (m, 2H), 3.28-3.31 (m, 2H), 3.06-3.09 (m, 2H), 2.67-2.70 (m, 2H), 2.29 (s, 3H).

Example 2-26

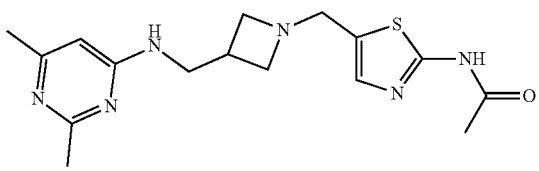 [SMILES: CC(=O)Nc1ncc(CN2CC(CNc3cc(C)nc(C)n3)C2)s1]

N-(5-((3-(((2,6-dimethylpyrimidin-4-yl)amino)methyl) azetidin-1-yl)methyl)thiazol-2-yl)acetamide: The title compound was prepared in an analogous manner of that in scheme 2 from 4-chloro-2,6-dimethylpyrimidine, tert-butyl 3-(aminomethyl)azetidine-1-carboxylate and N-(5-formylthiazol-2-yl)acetamide. LCMS (ESI): [M+H] 347. $^1$HNMR: (400 MHz, CD$_3$OD) δ 10.27 (br s, 1H), 7.19 (s, 1H), 6.04 (s, 1H), 5.24 (s, 1H), 3.71 (s, 2H), 3.45-3.53 (m, 2H), 3.35 (t, J=7.5 Hz, 2H), 3.05-3.08 (m, 2H), 2.67-2.71 (m, 1H), 2.47 (s, 3H), 2.33 (s, 3H), 2.27 (s, 3H).

Example 2-27

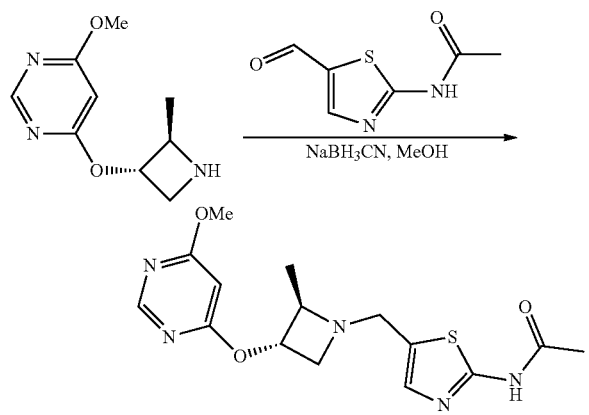

N-(5-(((2R,3S)-3-((6-methoxypyrimidin-4-yl)oxy)-2-methylazetidin-1-yl)methyl)thiazol-2-yl)acetamide: A solution of 4-methoxy-6-(((2R,3S)-2-methylazetidin-3-yl)oxy) pyrimidine (66 mg, 338.08 umol, 1 eq.) and N-(5-formylthiazol-2-yl)acetamide (58 mg, 338.08 umol, 1 eq.) in MeOH (4 mL) was stirred at 50° C. for 0.5 h. Sodium cyanoborohydride (64 mg, 1.01 mmol, 3 eq.) was added to the mixture. The reaction was stirred at 50° C. for 1 h. LCMS showed the desired product was detected. The reaction was concentrated to give a crude product, which was purified by pre-HPLC (Column: Waters Xbridge Prep OBD C18 100*19 5u, Conditions: water (0.04% NH$_3$H$_2$O+10 mM NH$_4$HCO$_3$)-ACN, Begin B: 15; End B: 45, Gradient Time (min): 10, 100% B Hold Time (min): 2, Flow Rate (ml/min): 25) to give N-(5-(((2R,3S)-3-((6-methoxypyrimidin-4-yl)oxy)-2-methylazetidin-1-yl)methyl)thiazol-2-yl)acetamide (19.3 mg, 16% yield) as white solid. LCMS (ESI): [M+H] 350. $^1$HNMR: (400 MHz, CD$_3$OD) δ 8.34 (s, 1H), 7.28 (s, 1H), 6.14 (s, 1H), 4.82-4.85 (m, 1H), 3.90-3.92 (m, 4H), 3.89 (s, 3H), 3.76-3.83 (m, 2H), 3.32-3.38 (m, 1H), 2.92 (t, J=7.2 Hz, 1H), 2.19 (s, 3H), 1.24 (d, J=6.4 Hz, 3H).

Example 2-28

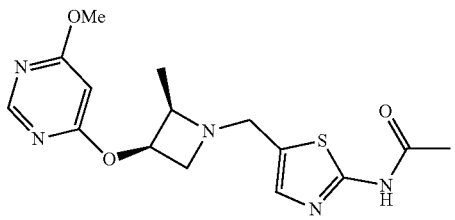 [SMILES: COc1cc(O[C@@H]2CN(Cc3cnc(NC(C)=O)s3)[C@@H]2C)ncn1]

N-(5-(((2R,3R)-3-((6-methoxypyrimidin-4-yl)oxy)-2-methylazetidin-1-yl)methyl)thiazol-2-yl)acetamide: The title compound was prepared in an analogous manner of that in scheme 3 from 4-chloro-6-methoxypyrimidine, tert-butyl 3-hydroxy-2-methylazetidine-1-carboxylate (and N-(5-formylthiazol-2-yl)acetamide. LCMS (ESI): [M+H] 350. $^1$HNMR: (400 MHz, CD$_3$OD) δ 8.33 (s, 1H), 7.28 (s, 1H), 6.22 (d, J=0.8 Hz, 1H), 5.36-5.40 (m, 1H), 3.87-3.93 (m, 4H), 3.41-3.79 (m, 2H), 3.42 (d, J=5.2 Hz, 2H), 2.19 (s, 3H), 1.06 (d, J=6.8 Hz, 3H).

Example 2-29

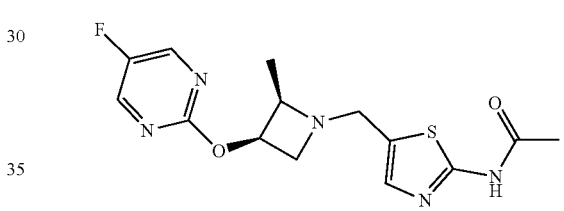

N-(5-(((2R,3R)-3-((5-fluoropyrimidin-2-yl)oxy)-2-methylazetidin-1-yl)methyl)thiazol-2-yl)acetamide: The title compound was prepared in an analogous manner of that in scheme 3 from 2-bromo-5-fluoropyrimidine, tert-butyl 3-hydroxy-2-methylazetidine-1-carboxylate and N-(5-formylthiazol-2-yl)acetamide. LCMS (ESI): [M+H] 338. $^1$HNMR: (400 MHz, CDCl$_3$) δ 11.62 (br s, 1H), 8.34 (s, 2H), 7.23 (s, 1H), 5.23-5.27 (m, 1H), 3.85-3.88 (m, 1H), 3.73-3.78 (m, 2H), 3.52-3.53 (m, 1H), 3.39-3.42 (m, 1H), 2.30 (s, 3H), 1.17 (d, J=6.0 Hz, 3H).

Example 2-30

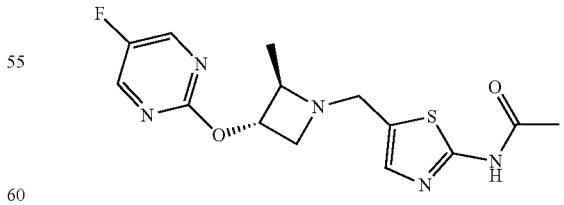

N-(5-(((2R,3S)-3-((5-fluoropyrimidin-2-yl)oxy)-2-methylazetidin-1-yl)methyl)thiazol-2-yl)acetamide: The title compound was prepared in an analogous manner of that in scheme 3 from 2-bromo-5-fluoropyrimidine, tert-butyl 3-hydroxy-2-methylazetidine-1-carboxylate and N-(5-formylthiazol-2-yl)acetamide. LCMS (ESI): [M+H] 338. $^1$HNMR:

(400 MHz, CDCl₃) δ11.39 (br s, 1H), 8.35 (s, 2H), 7.22 (s, 1H), 4.79-4.84 (m, 1H), 3.87-3.94 (m, 2H), 3.71-3.75 (m, 1H), 3.33-3.38 (m, 1H), 2.90 (t, J=7.2 Hz, 1H), 2.30 (s, 3H), 1.29 (d, J=6.4 Hz, 3H).

Example 2-31

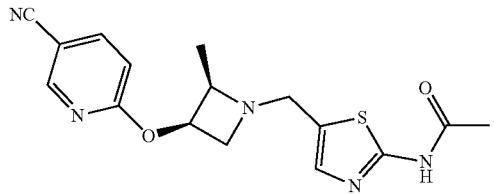 [SMILES: CC(=O)Nc1ncc(CN2C[C@@H](Oc3ccc(C#N)cn3)[C@H]2C)s1]

N-(5-(((2R,3R)-3-((5-cyanopyridin-2-yl)oxy)-2-methylazetidin-1-yl)methyl)thiazol-2-yl)acetamide: The title compound was prepared in an analogous manner of that in scheme 3 from 6-chloronicotinonitrile, tert-butyl 3-hydroxy-2-methylazetidine-1-carboxylate and N-(5-formylthiazol-2-yl)acetamide. LCMS (ESI): [M+H] 344. ¹HNMR: (400 MHz, CD₃OD) δ: 8.50 (s, 1H), 7.96 (dd, J=8.8, 2.4 Hz, 1H), 7.28 (s, 1H), 6.91 (d, J=8.8 Hz, 1H), 3.92-3.96 (m, 1H), 3.77-3.85 (m, 2H), 3.36-3.47 (m, 2H), 2.92-2.96 (m, 1H), 2.19 (s, 3H), 1.26 (d, J=6.4 Hz, 3H).

Example 2-32

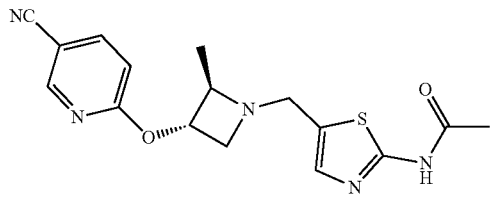 [SMILES: CC(=O)Nc1ncc(CN2C[C@H](Oc3ccc(C#N)cn3)[C@H]2C)s1]

N-(5-(((2R,3S)-3-((5-cyanopyridin-2-yl)oxy)-2-methylazetidin-1-yl)methyl)thiazol-2-yl)acetamide: The title compound was prepared in an analogous manner of that in scheme 3 from 6-chloronicotinonitrile, tert-butyl 3-hydroxy-2-methylazetidine-1-carboxylate and N-(5-formylthiazol-2-yl)acetamide. LCMS (ESI): [M+H] 344. ¹HNMR: (400 MHz, CD₃OD) δ: 8.50 (s, 1H), 7.96 (dd, J=8.8, 2.4 Hz, 1H), 7.28 (s, 1H), 6.91 (d, J=8.8 Hz, 1H), 3.92-3.96 (m, 1H), 3.77-3.85 (m, 2H), 3.36-3.47 (m, 2H), 2.92-2.96 (m, 1H), 2.19 (s, 3H), 1.26 (d, J=6.4 Hz, 3H).

Example 2-33

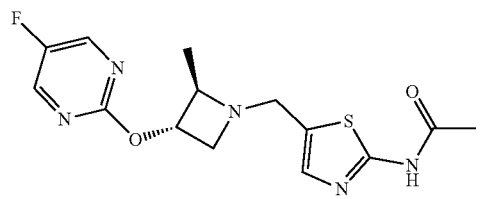 [SMILES: CC(=O)Nc1ncc(CN2C[C@H](Oc3ncc(F)cn3)[C@H]2C)s1]

N-(5-(((2R,3S)-3-((5-fluoropyrimidin-2-yl)oxy)-2-methylazetidin-1-yl)methyl)thiazol-2-yl)acetamide: The title compound was prepared in an analogous manner of that in scheme 3 from 2-bromo-5-fluoropyrimidine, tert-butyl 3-hydroxy-2-methylazetidine-1-carboxylate and N-(5-formylthiazol-2-yl)acetamide. LCMS (ESI): [M+H] 338. ¹HNMR: (400 MHz, CDCl₃) δ11.39 (br s, 1H), 8.35 (s, 2H), 7.22 (s, 1H), 4.79-4.84 (m, 1H), 3.87-3.94 (m, 2H), 3.71-3.75 (m, 1H), 3.33-3.38 (m, 1H), 2.90 (t, J=7.2 Hz, 1H), 2.30 (s, 3H), 1.29 (d, J=6.4 Hz, 3H).

Scheme 3

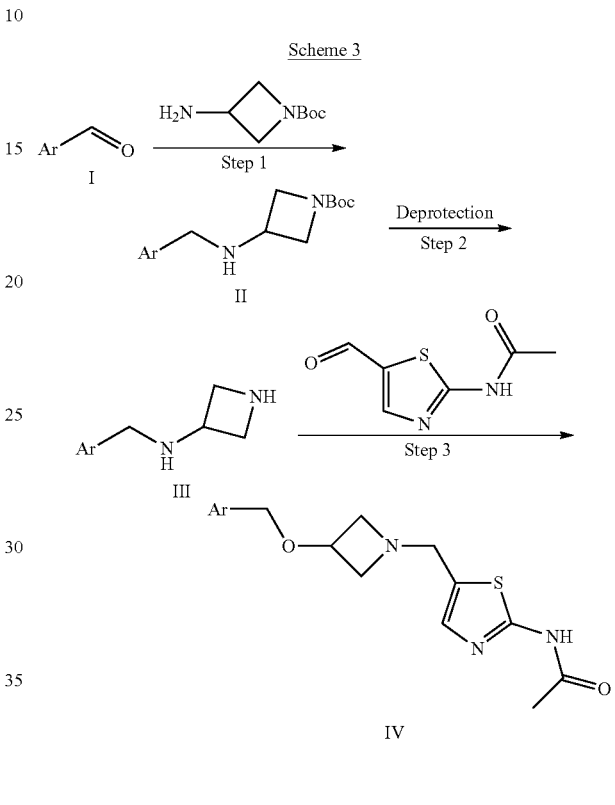

Intermediate 8

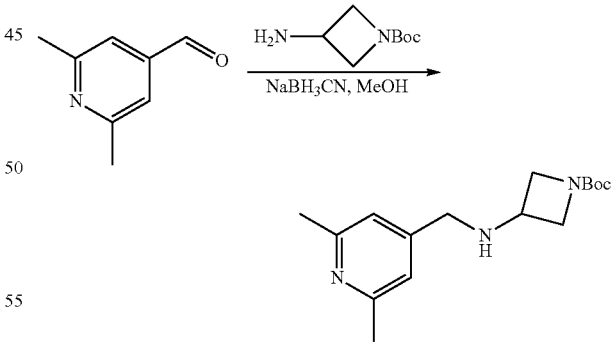

tert-butyl 3-(((2,6-dimethylpyridin-4-yl)methyl)amino)azetidine-1-carboxylate: A mixture of 2,6-dimethylisonicotinaldehyde (500 mg, 2.90 mmol, 1 eq.) and tert-butyl 3-aminoazetidine-1-carboxylate (431 mg, 3.19 mmol, 1.1 eq.) in MeOH (12 mL) was stirred for 30 min., and then sodium cyanoborohydride (547 mg, 8.70 mmol, 3 eq.) was added. The mixture was stirred at 30° C. for 2 hr. LCMS showed desired product was observed. The solvent was removed to give the residue, which was purified by column chromatography (EtOAc/MeOH=5/1) on silica gel to give tert-butyl 3-(((2,6-dimethylpyridin-4-yl)methyl)amino)azetidine-1-carboxylate (331.0 mg, 39% yield) as a yellow solid. LCMS (ESI): [M+H] 292. ¹HNMR: (500 MHz, CDCl₃) δ 6.91 (s, 2H), 4.07-4.10 (m, 2H), 3.64-3.66 (m, 4H), 3.58-3.61 (m, 1H), 2.51 (s, 6H), 1.4 (s, 9H).

Intermediate 9

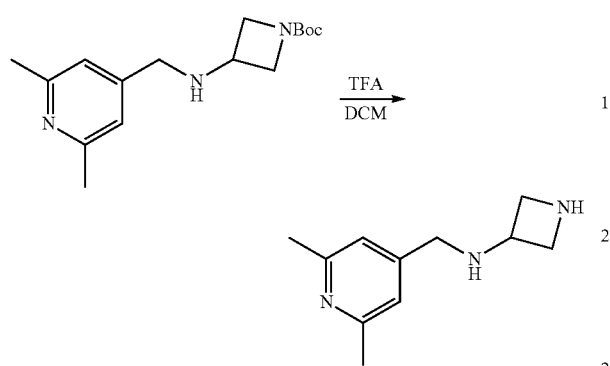

N-((2,6-dimethylpyridin-4-yl)methyl)azetidin-3-amine:
To a solution of tert-butyl 3-(((2,6-dimethylpyridin-4-yl)methyl)amino)azetidine-1-carboxylate (200 mg, 686.37 umol, 1 eq.) in DCM (10 mL) was added TFA (1 mL). The mixture was stirred at 25° C. for 2.0 hours. LCMS showed desired product was observed. The mixture was adjusted to pH 8~9 with ammonia. The mixture was concentrated to give N-((2,6-dimethylpyridin-4-yl)methyl)azetidin-3-amine (110 mg, crude) as a yellow solid. LCMS (ESI): [M+H] 192.

Example 3-1

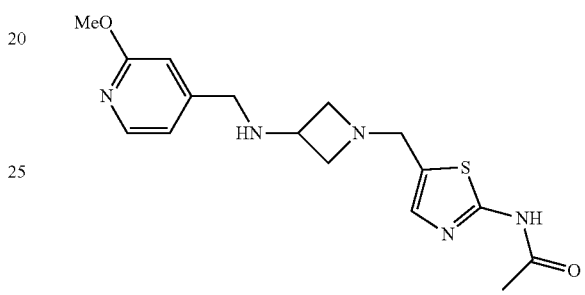

N-(5-((3-(((2,6-dimethylpyridin-4-yl)methyl)amino)azetidin-1-yl)methyl)thiazol-2-yl)acetamide: A mixture of N-((2,6-dimethylpyridin-4-yl)methyl)azetidin-3-amine (80 mg, 418.26 umol, 1 eq.) and N-(5-formylthiazol-2-yl)acetamide (142 mg, 836.51 umol, 2 eq.) in MeOH (10 mL) was stirred for 30 mins, and then sodium cyanoborohydride (78.9 mg, 1.25 mmol, 3 eq.) was added. The mixture was stirred at 30° C. for 2 hr. LCMS showed the desired product was observed. The mixture was purified by prepare HPLC (Column: Xtimate C18 150*25 mm*5 um; Condition: water (10 mM NH₄HCO₃)-ACN; Begin B: 11; End B: 41; Gradient Time (min): 10; 100% B Hold Time (min): 2; FlowRate (ml/min): 25) to give N-(5-((3-(((2,6-dimethylpyridin-4-yl)methyl)amino)azetidin-1-yl)methyl)thiazol-2-yl)acetamide (18.7 mg, 13% yield) as a yellow solid. LCMS (ESI): [M+H] 346. ¹HNMR: (500 MHz, CDCl₃) δ 11.56 (br s, 1H), 7.19 (s, 1H), 6.90 (s, 2H), 3.74 (s, 2H), 3.65 (s, 2H), 3.58-3.61 (m, 2H), 3.47-3.52 (m, 1H), 2.86-2.89 (m, 2H), 2.50 (s, 6H), 2.29 (s, 3H).

Example 3-2

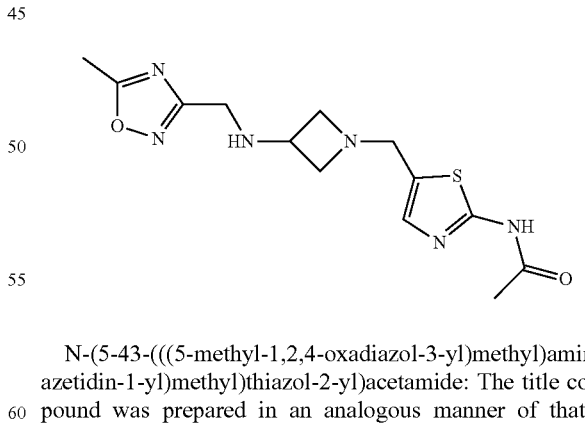

N-(5-((3-(((2-methoxypyridin-4-yl)methyl)amino)azetidin-1-yl)methyl)thiazol-2-yl)acetamide: The title compound was prepared in an analogous manner of that in scheme 4 from 2-methoxyisonicotinaldehyde, and tert-butyl 3-aminoazetidine-1-carboxylate and N-(5-formylthiazol-2-yl)acetamide. LCMS (ESI): [M+H] 348. ¹HNMR: (500 MHz, CDCl₃) δ 12.13 (br s, 1H), 8.08 (d, J=4.0 Hz, 1H), 7.18 (s, 1H), 6.80-6.82 (m, 1H), 6.67 (s, 1H), 3.91 (s, 3H), 3.72 (s, 2H), 3.68 (s, 2H), 3.56-3.59 (m, 2H), 3.47-3.51 (m, 1H), 2.82-2.85 (m, 2H), 2.29 (s, 3H).

Example 3-3

N-(5-43-(((5-methyl-1,2,4-oxadiazol-3-yl)methyl)amino)azetidin-1-yl)methyl)thiazol-2-yl)acetamide: The title compound was prepared in an analogous manner of that in scheme 4 from tert-butyl 3-(((5-methyl-1,2,4-oxadiazol-3-yl)methyl)amino)azetidine-1-carboxylate and N-(5-formylthiazol-2-yl)acetamide. LCMS (ESI): [M+H] 348. ¹HNMR: (500 MHz, CD₃OD) δ 7.27 (s, 1H), 6.55 (s, 1H), 4.46 (d, J=6.4 Hz, 2H), 3.81 (s, 2H), 3.47 (t, J=8.0 Hz, 2H), 3.19 (t, J=7.6 Hz, 2H), 2.89-2.96 (m, 1H), 2.51 (s, 3H), 2.38 (s, 3H), 2.19 (s, 3H).

Scheme 4

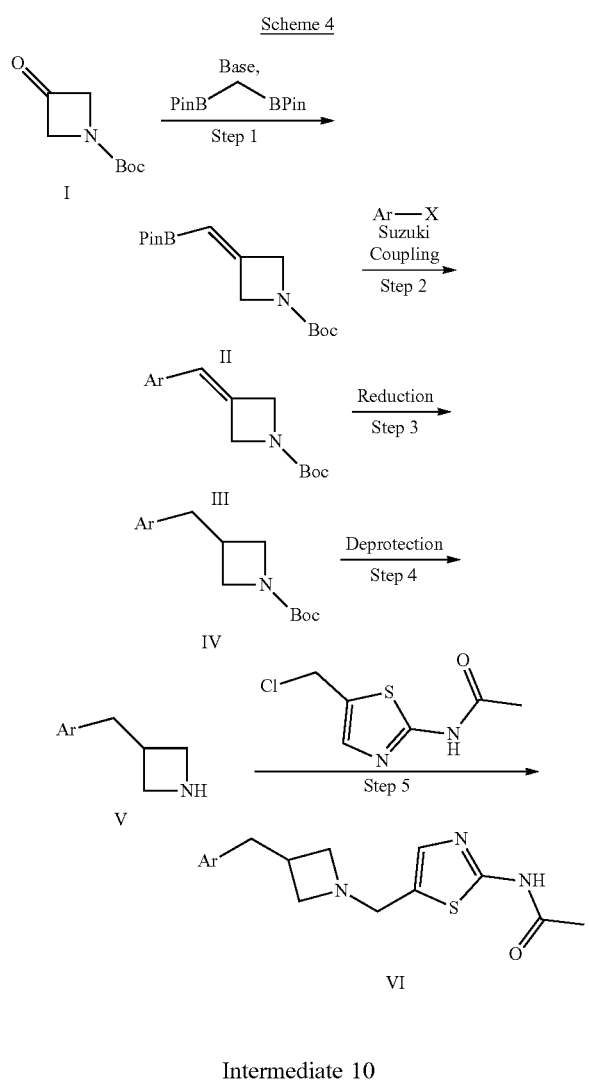

Intermediate 10 with ethyl acetate, dried over sodium sulfate, and concentrated. The crude organics were purified over silica eluting with heptanes/ethyl acetate (8:2) to afford tert-butyl 3-((4,4,5,5-tetramethyl-1,3,2-dioxaborolan-2-yl)methylene)azetidine-1-carboxylate (1.28 g) in 28% yield. LCMS (ESI): [M-t-Butyl] 240. $^1$HNMR: (500 MHz, CDCl$_3$) δ=4.64 (q, J=3.1 Hz, 2H), 4.48-4.57 (m, 2H), 1.47 (s, 9H), 1.25 ppm (s, 12H).

Intermediate 11

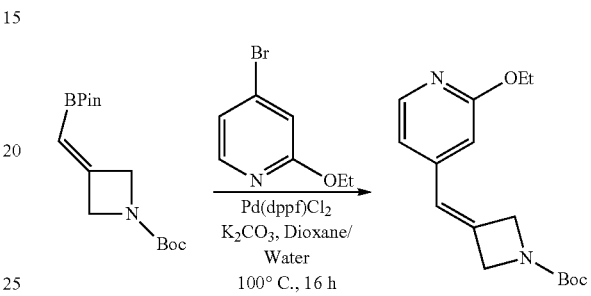

tert-butyl 3-((2-ethoxypyridin-4-yl)methylene)azetidine-1-carboxylate: A vessel was charged with tert-butyl 3-[(4,4,5,5-tetramethyl-1,3,2-dioxaborolan-2-yl)methylene]azetidine-1-carboxylate (216 mg, 731.76 umol), 4-bromo-2-ethoxy-pyridine (148 mg, 731.76 umol), potassium carbonate (303 mg, 2.20 mmol), Pd(dppf)Cl$_2$·DCM adduct (59.76 mg, 73.18 umol), Dioxane (3 mL) and water (1 mL). The mixture was heated to 100° C. and stirred for 16 h. The reaction was filtered over a pad of silica/celite and concentrated. The crude organics were passed over silica/celite and used directly in the next step without further purification. LCMS (ESI): [M+H] 291.

Intermediate 12

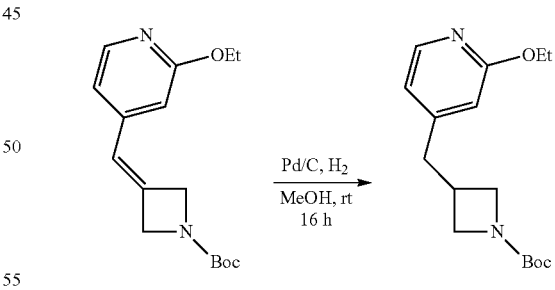

tert-butyl 3-((4,4,5,5-tetramethyl-1,3,2-dioxaborolan-2-yl)methylene)azetidine-1-carboxylate: A solution of 2,2,6,6-tetramethylpiperidine (2.6 g, 18.63 mmol, 3.13 mL) in THF (30 mL) was cooled to 0° C. n-BuLi (2.05 M, 10.92 mL) was added and the mixture was stirred for 10 min. A solution of 4,4,5,5-tetramethyl-2-[(4,4,5,5-tetramethyl-1,3,2-dioxaborolan-2-yl)methyl]-1,3,2-dioxaborolane (5 g, 18.63 mmol) in THF (6 mL) was added and the mixture was stirred for 15 min. The solution was cooled to −78° C. in a dry ice bath and tert-butyl 3-oxoazetidine-1-carboxylate (2.68 g, 15.66 mmol) in THF (15 mL) was added. The reaction was allowed to reach ambient temperature and was stirred for 16 h. The reaction was quenched with 30% K$_2$CO$_3$, extracted tert-butyl 3-((2-ethoxypyridin-4-yl)methyl)azetidine-1-carboxylate: A vessel was charged with tert-butyl 3-[(2-ethoxy-4-pyridyl)methylene]azetidine-1-carboxylate (212 mg, 730.13 umol), MeOH (5.00 mL) and Pd/C (78 mg, 73.01 umol, 10% purity). A balloon of H$_2$ was bubbled through the solution while venting and the reaction was stirred under H$_2$ for 16 h at rt. Upon completion, the reaction was filtered through celite and concentrated to afford tert-butyl 3-((2-ethoxypyridin-4-yl)methyl)azetidine-1-carboxylate (212 mg, 730.13 umol) which was carried directly to the next step without purification. LCMS (ESI): [M+H] 292.

Intermediate 13

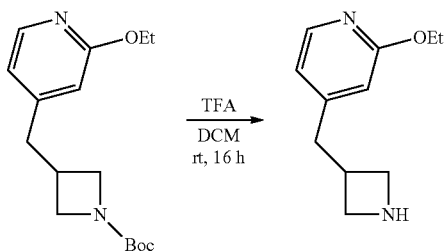 [SMILES: CCOc1cc(CC2CN(C(=O)OC(C)(C)C)C2)ccn1 ; CCOc1cc(CC2CNC2)ccn1]

4-(azetidin-3-ylmethyl)-2-ethoxy-pyridine:
tert-butyl 3-((2-ethoxypyridin-4-yl)methyl)azetidine-1-carboxylate (212 mg, 730.13 umol) was dissolved in DCM (5 mL) and TFA (166 mg, 1.46 mmol, 111.50 uL) was added. The reaction was stirred at rt for 16 h and then concentrated to afford the title compound (222.4 mg, 730.13 umol). LCMS (ESI): [M+H] 192.

Example 4-1

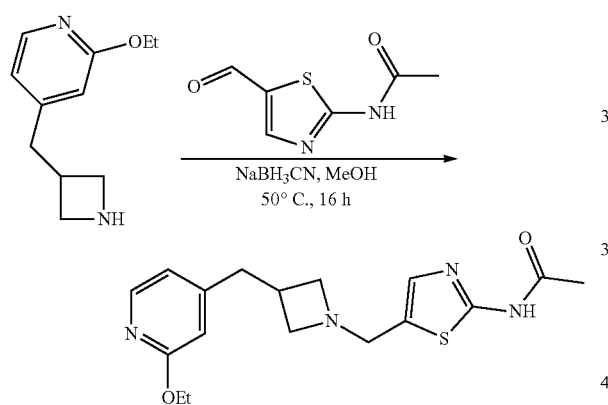

N-(5-((3-((2-ethoxypyridin-4-yl)methyl)azetidin-1-yl)methyl)thiazol-2-yl)acetamide:
4-(azetidin-3-ylmethyl)-2-ethoxy-pyridine was dissolved in MeOH (3 mL) and N-(5-formylthiazol-2-yl)acetamide (18 mg, 1.09 mmol) was added followed by sodium cyanoborohydride (92 mg, 1.46 mmol) and the mixture stirred at 50° C. for 16 h. The mixture was filtered over celite and purified over silica gel eluting with [EtOAc/EtOH (3:1)]/EtOAc (0→20→50%). LCMS (ESI): [M+H] 347. $^1$HNMR: (500 MHz, CD$_3$OD) δ=7.98 (d, J=5.5 Hz, 1H), 7.51-7.59 (m, 1H), 7.27 (s, 1H), 6.78 (d, J=5.4 Hz, 1H), 6.60 (s, 1H), 4.28 (q, J=7.3 Hz, 2H), 3.78 (s, 2H), 3.40-3.51 (m, 2H), 3.02 (dd, J=8.2, 6.4 Hz, 2H), 2.84-2.88 (m, 2H), 2.77-2.84 (m, 1H), 2.18-2.25 (m, 3H), 2.05 (s, 1H), 1.35-1.40 ppm (m, 3H).

Example 4-2

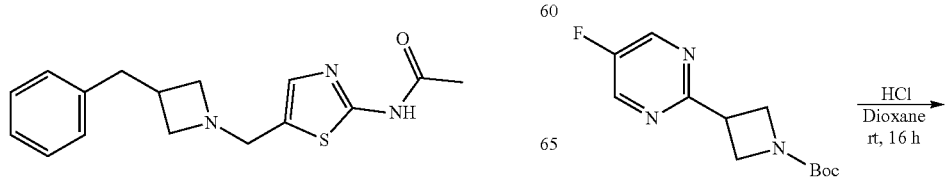

N-(5-((3-benzylazetidin-1-yl)methyl)thiazol-2-yl)acetamide:
The title compound was prepared in an analogous manner of that in Example 5-1 from tert-butyl 3-oxoazetidine-1-carboxylate and N-(5-formylthiazol-2-yl)acetamide. LCMS (ESI): [M+H] 302. $^1$HNMR: (500 MHz, CD$_3$OD) δ 7.29 (s, 1H), 7.03-7.41 (m, 5H), 3.84 (d, J=0.75 Hz, 2H), 3.43-3.55 (m, 2H), 3.10 (dd, J=6.78, 8.28 Hz, 2H), 2.71-2.90 (m, 3H), 2.21 (s, 3H).

Scheme 5

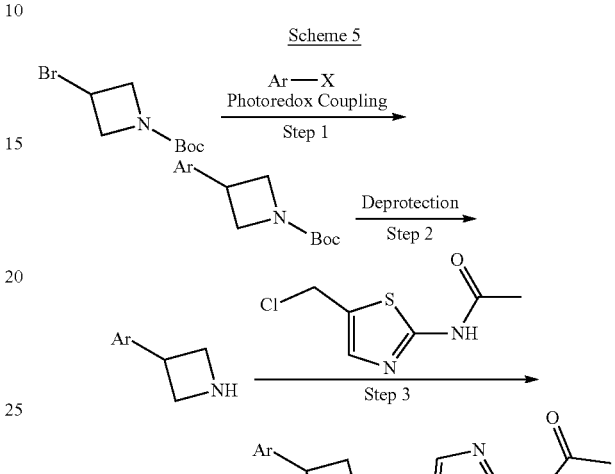

Intermediate 14

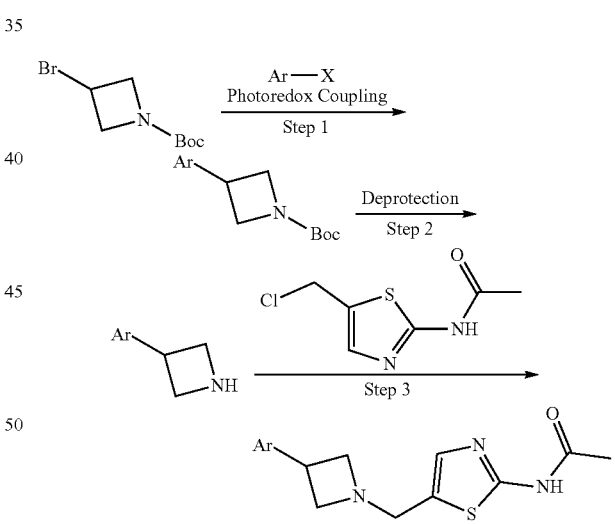

Intermediate 15

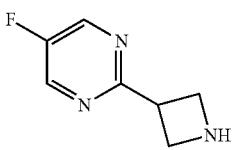

2-(azetidin-3-yl)-5-fluoropyrimidine: tert-butyl 3-(5-fluoropyrimidin-2-yl)azetidine-1-carboxylate (131 mg, 517 umol) was treated with HCl in dioxane (18 mg, 517 ul, 4M). The reaction was stirred for 16 h and the solvent was removed under reduced pressure to afford the title compound.

Example 5-1

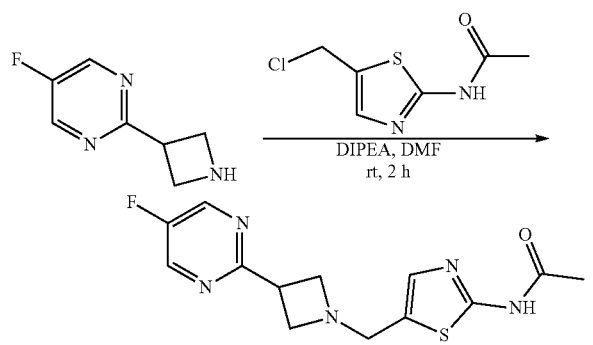

N-(5-43-(5-fluoropyrimidin-2-yl)azetidin-1-yl)methyl) thiazol-2-yl)acetamide: N-[5-(chloromethyl)thiazol-2-yl]acetamide (106 mg, 553.74 umol) was added to a solution of 2-(azetidin-3-yl)-5-fluoro-pyrimidine (105 mg, 553.74 umol, Hydrochloride) and Hunig's base (357 mg, 2.77 mmol, 483.55 uL) in DMF (2 mL). After 2 h, the solvent was removed under reduced pressure. The residue was dissolved in DCM, washed (NaHCO$_3$), dried over sodium sulfate and concentrated. The residue was purified over silica gel eluting with DCM/MeOH (8.5:1.5) to afford the title compound as an off white solid. LCMS (ESI): [M+H] 307. $^1$HNMR: (500 MHz, CDCl$_3$) δ 12.07 (br s, 1H), 8.47-8.64 (m, 2H), 7.25 (t, J=1.1 Hz, 1H), 4.03 (quin, J=7.7 Hz, 1H), 3.84 (s, 2H), 3.81 (t, J=7.8 Hz, 2H), 3.52 (t, J=7.5 Hz, 2H), 2.28-2.34 (m, 3H).

Example 5-2

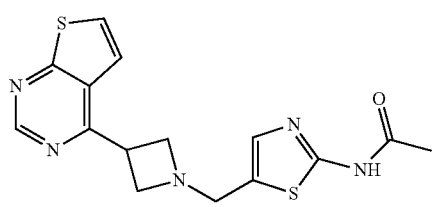 [SMILES: CC(=O)Nc1ncc(CN2CC(c3ncnc4sccc34)C2)s1]

N-(5-43-(thieno[2,3-d]pyrimidin-4-yl)azetidin-1-yl) methyl)thiazol-2-yl)acetamide: The title compound was prepared in an analogous manner of that in Example 6-1 from 4-tert-butyl-2-(4-tert-butyl-2-pyridyl)pyridine, 4-bromothieno[2,3-d]pyrimidine and N-[5-(chloromethyl)thiazol-2-yl]acetamide. LCMS (ESI): [M+H] 292. $^1$HNMR: (500 MHz, (CD$_3$)$_2$SO) δ 11.94 (s, 1H), 9.06 (s, 1H), 7.94 (d, J=6.0 Hz, 1H), 7.64 (d, J=6.1 Hz, 1H), 7.28 (s, 1H), 4.37 (quin, J=7.9 Hz, 2H), 3.70-3.78 (m, 6H), 3.44 (t, J=7.6 Hz, 3H), 2.11 (s, 4H).

Biological Data

OGA Enzyme Inhibition Biochemical Assay

Recombinant full length human OGA enzyme was purchased from Origene. 4-MUGlCNAc substrate was purchased from Sigma. All other reagents were purchased from Sigma or Fisher. Assay buffer consists of the McIlvaine buffer system, pH 6.4 (0.2M Na$_2$HPO$_4$ mixed with 0.1M citric acid) and 0.01% BSA. Reactions consist of 1 nM OGA, 100 μM 4-MUGlcNAc (K$_m$), and compound in a final volume of 10 μl. Reactions were incubated for 90 minutes at room temperature and quenched with 400 of 3M glycine, pH 10 and read on a Perkin Elmer Envision plate reader (Ex: 355 nm/Em: 460 nm). Compounds were tested with a 10-point dose-response starting from 20 μM with a 4-fold dilution. Data was fit using GraphPad Prism using a 4-parameter fit with variable slope.

| | OGA IC$_{50}$ (nM) |
|---|---|
| Example 1-1 | 91 |
| Example 1-2 | 480 |
| Example 1-3 | 220 |
| Example 2-1 | 407 |
| Example 2-2 | 530 |
| Example 2-3 | 160 |
| Example 2-4 | >20 |
| Example 2-5 | 340 |
| Example 2-6 | 170 |
| Example 2-7 | 210 |
| Example 2-8 | 450 |
| Example 2-9 | 170 |
| Example 2-10 | 600 |
| Example 2-11 | 407 |
| Example 2-12 | 33 |
| Example 2-13 | 59 |
| Example 2-14 | 130 |
| Example 2-15 | 800 |
| Example 2-16 | 570 |
| Example 2-17 | 11 |
| Example 2-18 | 570 |
| Example 2-19 | 25 |
| Example 2-20 | 480 |
| Example 2-21 | 1300 |
| Example 2-22 | 1500 |
| Example 2-23 | 670 |
| Example 2-24 | 1400 |
| Example 2-25 | 610 |
| Example 2-26 | 1300 |
| Example 2-27 | 600 |
| Example 2-28 | 110 |
| Example 2-29 | 570 |
| Example 2-30 | 170 |
| Example 2-31 | 440 |
| Example 2-32 | 980 |
| Example 2-33 | 390 |
| Example 3-1 | 91 |
| Example 3-2 | 210 |
| Example 3-3 | 900 |
| Example 4-1 | 47 |
| Example 4-2 | 580 |
| Example 5-1 | 350 |
| Example 5-2 | 194 |

While we have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound represented by the following structural formula:

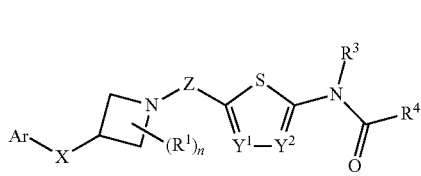

(I)

or a pharmaceutically acceptable salt thereof, wherein:
- Ar is an optionally substituted 6- to 10-membered aryl or an optionally substituted 5- to 10-membered heteroaryl;
- X is —$CR^2R^2$—, —$(CR^2R^2)O$—, —$NR^d$—, or —$NR^d(CR^2R^2)$;
- $Y^1$ and $Y^2$ are each $CR^c$ or N, wherein at least one of $Y^1$ or $Y^2$ is N;
- Z is —$CR^2R^2$—, —C(=O)—, —$(CR^2R^2)_2$—, or —$CH_2C(=O)$—;
- $R^c$ is —H, halo, —$C_1$-$C_4$ alkyl, or —$C_1$-$C_4$ haloalkyl;
- $R^d$ is —H or —$C_1$-$C_4$ alkyl;
- n is 0 or an integer from 1 to 5;
- when n is other than 0, $R^1$, for each occurrence, is independently halo, —$C_1$-$C_4$ alkyl, —$C_1$-$C_4$ haloalkyl, or —$C_1$-$C_4$ alkoxy;
- $R^2$, for each occurrence, is independently —H, halo, —$C_1$-$C_4$ alkyl, —$C_1$-$C_4$ haloalkyl, —$C_3$-$C_{10}$ cycloalkyl, or —$C_3$-$C_{10}$ halocycloalkyl;
- or alternatively two $R^2$ together with the carbon atom to which they are attached form a —$C_3$-$C_{10}$ cycloalkyl;
- $R^3$ is —H or —$C_1$-$C_4$ alkyl; and
- $R^4$ is —H, —$C_1$-$C_4$ alkyl, —$C_1$-$C_4$ haloalkyl, or —$C_3$-$C_6$ cycloalkyl;
- or alternatively $R^3$ and $R^4$ taken together with their intervening atoms form an optionally substituted 5- to 7-membered heterocyclyl.

2. The compound according to claim 1, wherein the compound is represented by the following structural formula:

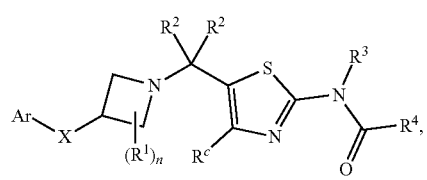

(II)

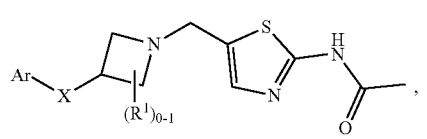

(III)

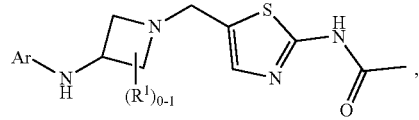

(IV-A)

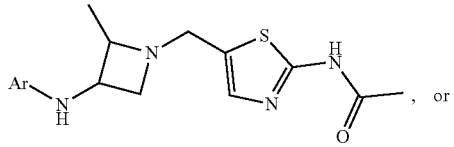

(IV-B)

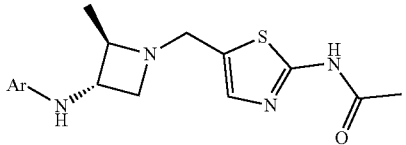

(V)

or a pharmaceutically acceptable salt thereof.

3. The compound according to claim 1, or a pharmaceutically acceptable salt thereof, wherein $R^c$ is —H or halo and $R^4$ is —H and —$C_1$-$C_4$ alkyl.

4. The compound according to claim 1, wherein Ar is an optionally substituted 5- to 10-membered heteroaryl.

5. The compound according to claim 1, wherein Ar is an optionally substituted 5- or 6-membered monocyclic heteroaryl.

6. The compound according to claim 1, wherein Ar is an optionally substituted 6-membered monocyclic heteroaryl.

7. The compound according to claim 1 or a pharmaceutically acceptable salt thereof, wherein Ar is an optionally substituted pyridinyl, an optionally substituted pyrimidinyl, or an optionally substituted pyrazinyl.

8. The compound according to claim 1 or a pharmaceutically acceptable salt thereof, wherein Ar is an optionally substituted

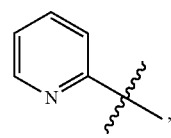 [SMILES: *c1ccccn1]

an optionally substituted

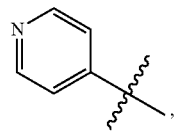

an optionally substituted

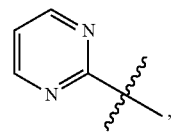 [SMILES: *c1ncccn1]

an optionally substituted

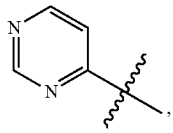, an optionally substituted

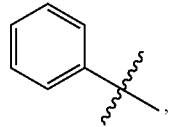 [SMILES: *c1ccccc1], an optionally substituted

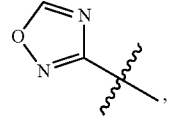 [SMILES: *c1ncon1], or an optionally substituted

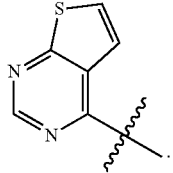.

9. The compound according to claim 1 or a pharmaceutically acceptable salt thereof, wherein Ar is an optionally substituted

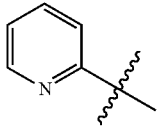 [SMILES: *c1ccccn1]

or an optionally substituted

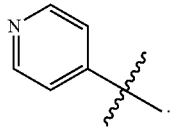.

10. The compound according to claim 1 or a pharmaceutically acceptable salt thereof, wherein Ar is optionally substituted with one or more groups selected from $C_1$-$C_4$ alkyl, $C_1$-$C_4$ haloalkyl, $C_3$-$C_6$ cycloalkyl, $C_3$-$C_6$ heterocyclyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S) NR$^x$R$^y$, —C(=S)R$^x$, —C(=O)R$^x$, phenyl and monocyclic heteroaryl;

wherein the $C_1$-$C_4$ alkyl group substituent on Ar is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O) OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^y$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy);

the $C_3$-$C_6$ cycloalkyl, $C_3$-$C_6$ heterocyclyl, phenyl and monocyclic heteroaryl group substituent on Ar are optionally and independently substituted with $C_1$-$C_4$ alkyl, $C_1$-$C_4$ haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S) OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$;

each R$^x$ and each R$^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by R$^x$ or R$^y$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy or halomethoxy);

R$^z$ is —H, $C_1$-$C_4$ alkyl, $C_1$-$C_4$ alkoxy, $C_3$-$C_8$ cycloalkyl, or $C_3$-$C_8$ heterocyclyl; wherein the $C_1$-$C_4$ alkyl or $C_3$-$C_8$ cycloalkyl group represented by R$^z$ is optionally substituted with one or more substituents selected from —CN, halo, hydroxyl, $C_1$-$C_4$ alkyl, $C_1$-$C_4$ alkoxy, $C_3$-$C_6$ cycloalkyl and phenyl (optionally substituted with one or more groups selected from —CH$_3$, halomethyl, halo, methoxy and halomethoxy); and i is 0, 1, or 2.

11. The compound according to claim 1 or a pharmaceutically acceptable salt thereof, wherein Ar is optionally substituted with one or more groups selected from $C_1$-$C_4$ alkyl, $C_1$-$C_4$ haloalkyl, halo, —CN, —NO$_2$, —OR$^z$, —SR$^z$, —NR$^x$S(O)$_i$R$^y$, —C(=O)OR$^x$, —OC(=O)OR$^x$, —C(=S) OR$^y$, —O(C=S)R$^x$, —C(=O)NR$^x$R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O) NR$^x$R$^y$, —NR$^x$(C=S)NR$^x$R$^y$, —C(=S)R$^x$, and —C(=O) R$^x$; wherein each R$^x$, each R$^y$ and R$^z$ each is independently —H or $C_1$-$C_4$ alkyl.

12. The compound according to claim 1 or a pharmaceutically acceptable salt thereof, wherein Ar is optionally substituted with one or more groups selected from $C_1$-$C_4$ alkyl, $C_1$-$C_4$ haloalkyl, halo, —CN, —OR$^z$, and —C(=O) NR$^x$R$^y$ wherein each R$^x$, each R$^y$ and each R$^z$ each is independently —H or $C_1$-$C_4$ alkyl.

13. The compound according to claim 1 or a pharmaceutically acceptable salt thereof, wherein Ar is optionally substituted with one or more groups selected from —CH₃, —F, —CN, and —OCH₃.

14. A pharmaceutical composition comprising the compound according to claim 1 or a pharmaceutically acceptable salt thereof and a pharmaceutically acceptable carrier or diluent.

15. A method of treating a subject with a disease or condition that is caused, mediated and/or propagated by O-GlcNAcase activity selected from a neurodegenerative disease, a tauopathy, diabetes, cancer and stress, comprising administering to the subject an effective amount of the compound according to claim 1.

16. The method according to claim 15, wherein the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease type C, Pallido-ponto-nigral degeneration, Parkinsonism-dementia complex of Guam, Pick's disease (PiD), Postencephalitic parkinsonism (PEP), Prion diseases, Subacute sclerosing panencephalitis, Tangle-only dementia, Huntington's disease, and Parkinson's disease.

17. The method according to claim 14, wherein the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, ischemic stroke, mild cognitive impairment (MCI), Huntington's disease, and Parkinson's disease.

18. The method according to claim 14, wherein the disease or condition is Alzheimer's disease.

19. A method of inhibiting O-GlcNAcase in a subject in need thereof, comprising:
    administering to the subject an effective amount of the compound according to claim 1.

20. A method of treating a disease or condition characterized by hyperphosphorylation of tau in the brain, comprising administering to the subject an effective amount of the compound according to claim 1.

* * * * *